(12) United States Patent
Wong et al.

(10) Patent No.: US 9,267,175 B2
(45) Date of Patent: Feb. 23, 2016

(54) MULTI-BIOMARKER-BASED OUTCOME RISK STRATIFICATION MODEL FOR ADULT SEPTIC SHOCK

(71) Applicant: CHILDREN'S HOSPITAL MEDICAL CENTER, Cincinnati, OH (US)

(72) Inventors: Hector R. Wong, Cincinnati, OH (US); Christopher John Lindsell, Cincinnati, OH (US)

(73) Assignee: Children's Hospital Medical Center, Cincinnati, OH (US)

( * ) Notice: Subject to any disclaimer, the term of this patent is extended or adjusted under 35 U.S.C. 154(b) by 0 days.

(21) Appl. No.: 14/377,153

(22) PCT Filed: Feb. 7, 2013

(86) PCT No.: PCT/US2013/025221
§ 371 (c)(1),
(2) Date: Aug. 6, 2014

(87) PCT Pub. No.: WO2013/119869
PCT Pub. Date: Aug. 15, 2013

(65) Prior Publication Data
US 2015/0005189 A1 Jan. 1, 2015

Related U.S. Application Data

(60) Provisional application No. 61/721,705, filed on Nov. 2, 2012, provisional application No. 61/595,996, filed on Feb. 7, 2012.

(51) Int. Cl.
*G01N 31/00* (2006.01)
*G01N 33/53* (2006.01)
*C12Q 1/68* (2006.01)
*G01N 33/68* (2006.01)

(52) U.S. Cl.
CPC .............. *C12Q 1/6883* (2013.01); *G01N 33/68* (2013.01); *C12Q 2600/112* (2013.01); *C12Q 2600/158* (2013.01); *G01N 2800/26* (2013.01); *G01N 2800/52* (2013.01); *G01N 2800/54* (2013.01)

(58) Field of Classification Search
CPC ............. A61K 2300/00; C12Q 1/6883; C12Q 2563/143; C12Q 2565/633; G01N 33/6893; G01N 2800/26
See application file for complete search history.

(56) References Cited

U.S. PATENT DOCUMENTS

| 7,645,573 B2 | 1/2010 | Ivey et al. |
|---|---|---|
| 2003/0194752 A1 | 10/2003 | Anderson et al. |
| 2004/0121343 A1 | 6/2004 | Buechler et al. |
| 2010/0279878 A1 | 11/2010 | Wong |
| 2011/0059858 A1 | 3/2011 | Kas et al. |
| 2011/0312521 A1 | 12/2011 | Chaussabel |
| 2015/0018238 A1 | 1/2015 | Wong et al. |

FOREIGN PATENT DOCUMENTS

| EP | 2085486 A1 | 8/2009 |
|---|---|---|
| WO | WO-2006/113833 A2 | 10/2006 |
| WO | WO 2009-095786 | 8/2009 |
| WO | WO 2009-095840 | 8/2009 |
| WO | WO-2012/106396 A2 | 8/2012 |
| WO | WO-2013/119871 A1 | 8/2013 |

OTHER PUBLICATIONS

Kaplan et. al. (Pediatric Critical Care Medicine, Mar. 2011, 12(2), pp. 165-173).*
Standage and Wong (Expert Rev. Anti. Infect. Ther, Jan. 2011, 9(1) pp. 71-79).*
Aneja and Carcillo (Minerva Anestesiol, 2011, 77, pp. 986-992).*
Alder et al., "The pediatric sepsis biomarker risk model: potential implications for sepsis therapy and biology," Expet Rev. Anti Infect. Ther., 2014, pp. 809-816, vol. 12(7).
Brierley et al., "Clinical practice parameters for hemodynamic support of pediatric and neonatal septic shock: 2007 update from the American College of Critical Care Medicine," Crit. Care Med., 2009, pp. 666-688, vol. 37(2).
Che et al., "Decision tree and ensemble learning algorithms with their applications in bioinformatics," Adv. Exp. Med. Biol., 2011, 191-199, vol. 696.
Cornell et al., "Mechanisms and regulation of the gene-expression response to sepsis," Pediatrics., Jun. 2010, pp. 1248-1258, vol. 125(6).
Cvijanovich et al., "Validating the genomic signature of pediatric septic shock," Physiol. Genomics., Jun. 12, 2008, pp. 127-134, vol. 34(1).
Dellinger et al., "Surviving Sepsis Campaign: international guidelines for management of severe sepsis and septic shock: 2008," A26.
Dellinger et al., "Surviving sepsis campaign: international guidelines for management of severe sepsis and septic shock: 2012," Crit. Care Med., Feb. 2013, pp. 580-637, vol. 41(2).
Dombrovskiy et al., "Rapid increase in hospitalization and mortality rates for severe sepsis in the United States: a trend analysis from 1993 to 2003," Crit. Care Med., May 2007, pp. 1244-1250, vol. 35(5).
Hanley et al., "A method of comparing the areas under receiver operating characteristic curves derived from the same cases," Radiology, Sep. 1983, pp. 839-843, vol. 148(3).
Kaplan et al., "Biomarker discovery and development in pediatric critical care medicine," Pediatr. Crit. Care Med., Mar. 2011, pp. 165-173, vol. 12(2).
Levy et al., "The Surviving Sepsis Campaign: results of an international guideline-based performance improvement program targeting severe sepsis," Crit. Care Med., Feb. 2010, pp. 367-374, vol. 38(2).
Marshall, "Sepsis: rethinking the approach to clinical research," J. Leukoc. Biol., Mar. 2008, 471-482, vol. 83(3).
Maslove et al., "Gene expression profiling in sepsis: timing, tissue, and translational considerations," Trends in Molecular Medicine, Apr. 2014, pp. 204-213, vol. 20(4).

(Continued)

*Primary Examiner* — Lisa Cook
(74) *Attorney, Agent, or Firm* — Mintz Levin Cohn Ferris Glovsky and Popeo, P.C.; Muriel Liberto, Esq.

(57) ABSTRACT

The invention provides a multi-biomarker based methods to stratify adult septic shock patients into high and low risk groups.

8 Claims, 5 Drawing Sheets

(56) References Cited

OTHER PUBLICATIONS

Muller et al., "Logistic regression and CART in the analysis of multimarker studies," Clin. Chim. Acta., Aug. 2008, pp. 1-6, vol. 394(1-2).
Nichol et al., "Relative hyperlactatemia and hospital mortality in critically ill patients: a retrospective multi-centre study," Crit. Care. 2010, p. R25, vol. 14(1).
Osuchowski et al., "Stratification is the key: inflammatory biomarkers accurately direct immunomodulatory therapy in experimental sepsis," Crit. Care Med., May 2009, pp. 1567-1573, vol. 37(5).
Ranieri et al., "Drotrecogin alfa (activated) in adults with septic shock," N. Engl. J. Med., May 31, 2012, pp. 2055-2064, vol. 366(22).
Russell et al., "Vasopressin versus norepinephrine infusion in patients with septic shock," N. Engl. J. Med., Feb. 28, 2008, pp. 877-887, vol. 358(9).
Vincent et al., "Ten reasons why we should NOT use severity scores as entry criteria for clinical trials or in our treatment decisions," Crit. Care Med., Jan. 2010, pp. 283-287, vol. 38(1).
Wacharasint et al., "Normal-range blood lactate concentration in septic shock is prognostic and predictive," Shock, Jul. 2012, pp. 4-10, vol. 38(1).
Wong et al., "A Multibiomarker-Based Outcome Risk Stratification Model for Adult Septic Shock," Critical Care Medicine, Apr. 2014, pp. 781-789, vol. 42(4).
Wong et al., "Genome-level expression profiles in pediatric septic shock indicate a role for altered zinc homeostasis in poor outcome," Physiol. Genomics., Jul. 18, 2007, pp. 146-55, vol. 30(2).
Wong et al., "Genomic expression profiling across the pediatric systemic inflammatory response syndrome, sepsis, and septic shock spectrum," Crit. Care Med., May 2009, pp. 1558-1566, vol. 37(5).
Wong et al., "Testing the Prognostic Accuracy of the Updated Pediatric Sepsis Biomarker Risk Model," PLoS ONE, Jan. 2014, pp. e86242 (6 pgs.), vol. 9(1).
Wong et al., "The pediatric sepsis biomarker risk model," Crit. Care., Oct. 1, 2012, p. R174, vol. 16(5).
Wong et al., "The Temporal Version of the Pediatric Sepsis Biomarker Risk Model," PLoS ONE, Mar. 2014, pp. e92121 (7 pgs.), vol. 9(3).
Wynn et al., "The host response to sepsis and developmental impact," Pediatrics., May 2010, pp. 1031-1041, vol. 125(5).
Doyuk Kartal Elif et al., "Sepsisli Hastalarin Degerlendirilmesinde Apache II Skorlama Sistemi ile Birlikte Sitokinler,Protein C Duzeyleri", Balkan Medical Journal, 174-178 (2012).
Hack et al., "Interleukin-8 in relation to shock and inflammatory mediators", Infection and Immunity, American Society for Microbiology, 60(7): 2835-2842 (1992).
Hein Ortrud Vargas et al., "Time course of endothelial damage in septic prediction of outcome", Critical Care, Biomed Central Ltd., 9(4): R307-R314 (2005).
Simona Mera et al., "Multiplex cytokine profiling in patients with sepsis", APMIS, 119(2):155-163 (2010).
Allen, T.C. et al. (Mar. 2007). "Anti-interleukin 8 autoantibody:interleukin 8 immune complexes visualized by laser confocal microscopy in injured lung," Arch Pathol Lab Med 131(3):452-456.
Hack, E. et al. (Jul. 1992). "Interleukin-8 in relation to shock and inflammatory mediators", Infection and Immunity, American Society for Microbiology: 60(7): 2835-2842.
Livaditi, O. et al. (Dec. 2006, e-published Mar. 26, 2007). "Neutrophil CD64 expression and serum IL-8: sensitive early markers of severity and outcome in sepsis," Cytokine 36(5-6):283-290.
Lokshin, A.E. et al. (Aug. 2006, e-published Jan. 24, 2006). "Circulating IL-8 and anti-IL-8 autoantibody in patients with ovarian cancer," Gynecol Oncol 12(2):244-251.
Verboon-Maciolek, M.A. et al. (Mar. 2006). "Inflammatory mediators for the diagnosis and treatment of sepsis in early infancy," Pediatr Res 59(3):457-461.
Vermont Clementien L et al: CC and CXC chemokine levels in children with meningococcal sepsis accurately mortality and disease severity', Critical Care, Biomed Central Ltd., 10(1):1-8 (2006).
Hector R Wong et al:"The pediatric sepsis biomarker risk model", Critical Care, Biomed Central Ltd., 16(5):1-9 (2012).
Allison et al., "Microarray data analysis: from disarray to consolidation and consensus," Nat. Rev. Genet., Jan. 2006, pp. 55-65, vol. 7(1) [abstract only].
Czaja et al., "Readmission and late mortality after pediatric severe sepsis," Pediatrics, Mar. 2009, pp. 849-857, vol. 123(3) [abstract only].
Freishtat et al., "Sepsis Alters the Megakaryocyte-Platelet Transcriptional Axis Resulting in Granzyme B-mediated Lymphotoxicity," Am. J. Respir. Crit. Care Med., 2009, pp. 467-473, vol. 179.
Giuliano et al., "Admission Angiopoietin Levels in Children with Septic Shock," Shock, Dec. 2007, pp. 650-654, vol. 28(6).
Goldstein et al. "International Pediatric Sepsis Consensus Conference: Definitions for Sepsis and Organ Dysfunction in Pediatrics," Pediatric Crit Care Med Jan 2005 pp2-8, vol. 6(1) [abstract only].
Kaplan et al., "Changes in peroxisome proliferator activated receptor-gamma activity in children with septic shock," Intensive Care Med., Jan. 2010, pp. 123-130, vol. 36(1).
Marshall et al., "Biomarkers of sepsis," Crit. Care Med., Jul. 2009, pp. 2290-2298, vol. 37(7) [abstract only].
Nadel et al. Drotrecogin alfa (activated) in children with severe sepsis: a multicenter phase III randomized controlled trial, Lancet, Mar 10, 2007, pp. 836-43, vol. 369(564)—abstract only.
Nowak et al., Admission Chemokine (C-C motif) Ligand 4 Levels Predict Survival in Pediatric Septic Shock, Pediatr. Crit. Care Med., Mar. 2010, pp. 213-216, vol. 11(2).
Patent Cooperation Treaty, "International Preliminary Report on Patentability and Written Opinion" in corresponding International application No. PCT/US2013/025223, mailed Aug. 12, 2014, 5 pgs.
Patent Cooperation Treaty, "International Search Report" in corresponding International application No. PCT/US2013/025223, mailed May 30, 2013, 2 pgs.
Pollack et al., "The Pediatric Risk of Mortality III-Acute Physiology Score (PRISM III-APS): a method of assessing physiologic instability for pediatric intensive care unit patients," J Pediatr., Oct. 1997, pp. 575-81, vol. 131(4) [abstract only].
Shanley et al., "Genome-Level Longitudinal Expression of Signaling Pathways and Gene Networks in Pediatric Septic Shock," Mol Med, Sep.-Oct. 2007, pp. 495-508, vol. 13(9-10).
Sharron et al., "Platelets Induce Apoptosis during Sepsis in a Contact-Dependent Manner That Is Inhibited by GPllb/llla Blockade," PLoS ONE, Jul. 2012, p. e41549, vol. 7(7).
Solan et al., "A novel role for matrix metalloproteinase-8 in sepsis," Crit Care Med., Feb. 2012, pp. 379-387, vol. 40(2).
Standage et al., Biomarkers for pediatric sepsis and septic shock, Expert Rev. Anti Infect. Ther., 2011, pp. 71-79.
Sweeney et al., "Recombinant human activated protein C, package labeling, and hemorrhage risks," Crit. Care Med., Jan. 2009, pp. 327-329, vol. 37(1).
Vincent, et al., "Ten reasons why we should not use severity scores as entry criteria for clinical trials or in our treatment decisions," Crit Care Med., Jan. 2010, pp. 283-7, vol. 38(1) [abstract only].
Watson et al., "Scope and epidemiology of pediatric sepsis," Pediatr Crit Care Med, 2005, vol. 6(3), (Suppl.).
Watson et al., "The Epidemiology of Severe Sepsis in Children in the United States," Am J Respir Crit Care Med, 2003, pp. 695-701, vol. 167.
Wheeler et al., "Extracellular heat shock protein 60 (Hsp60) levels in children with septic shock," Inflamm Res., May 2007, pp. 216-9, vol. 56(5) [abstract only].
Wheeler et al., "Extracellular hsp70 levels in children with septic shock," Pediatr Crit Care Med. May 2005, pp. 308-11 vol. 6(3) [abstract only].
Wheeler et al., "Serum Neutrophil Gelatinase-associated Lipocalin (NGAL) as a Marker of Acute Kidney Injury in Critically Iii Children with Septic Shock," Crit Care Med., Apr. 2008, pp. 1297-1303, vol. 36(4).
Wong et al., "Increased serum nitrite and nitrate concentrations in children with the sepsis syndrome,"Crit Care Med., May 1995, pp. 835-42, vol. 23(5) [abstract only].
Wong et al., "Plasma bactericidal/permeability-increasing protein concentrations in critically ill children with the sepsis syndrome,"Pediatr Infect Dis J., Dec. 1995, pp. 1087-91, vol. 14(12) [abstract only].
Wong, "Pediatric septic shock treatment: new clues from genomic profiling," Pharmacogenetics, Oct. 2007, pp. 128790, vol. 8(10).

\* cited by examiner

MULTI-BIOMARKER-BASED OUTCOME RISK STRATIFICATION MODEL FOR ADULT SEPTIC SHOCK

CROSS REFERENCE TO RELATED APPLICATION

The present application is a U.S. National Stage entry under 35 U.S.C. §371 of International Application No. PCT/US2013/025221, filed on Feb. 7, 2013, designating the United States of America and published in English on Aug. 15, 2013, which in turn claims the benefit of priority under 35 U.S.C. §119(e) to U.S. Provisional Application No. 61/595,996, BIOMARKERS OF SEPTIC SHOCK, filed on Feb. 7, 2012, and U.S. Provisional Application No. 61/721,705, A MULTI-BIOMARKER-BASED OUTCOME RISK STRATIFICATION MODEL FOR ADULT SEPTIC SHOCK, filed on Nov. 2, 2012, which are currently co-pending herewith and which are incorporated by reference in their entirety.

STATEMENT REGARDING FEDERALLY-SPONSORED RESEARCH

This invention was made with government support under HL100474, GM064619, GM099773, and RR026314 awarded by the National Institutes of Health. The government has certain rights in the invention.

FIELD OF THE INVENTION

The invention disclosed herein generally relates to the identification and validation of clinically relevant, quantifiable biomarkers of diagnostic and therapeutic responses for blood, vascular, cardiac, and respiratory tract dysfunction.

BACKGROUND

Septic shock and severe sepsis represent a major public health problem in the United States, despite the development of increasingly powerful antibiotics and advanced forms of intensive care unit-based support modalities (see, e.g., Shanley, T. et al. *Sepsis,* 3$^{rd}$ Ed., St. Louis, Mo., Mosby (2006)). Worldwide, septic shock affects millions of adults, killing approximately one in four (see, e.g., Dellinger, R. et al. *Crit. Care Med.* 36:296-327 (2008)). A recent study suggests that the incidence and the mortality rates of septic shock in adults are increasing in the United States (Dombrovskiy, V. et al. *Crit. Care Med.* 35:1244-50 (2007)).

Reliably stratifying patients into those at low risk and those at high risk for poor outcomes is fundamental to effective clinical practice and clinical research (Marshall *J. Leukoc. Biol.* 83:471-82 (2008)). No reliable and widely accepted risk stratification tool specific for septic shock in adults has heretofore been developed. Such a tool would be beneficial at several levels, including better-informed decision making for individual patients (i.e. prognostication), as an adjustment or design variable in interventional clinical trials, and as a metric for quality improvement efforts.

SUMMARY

Embodiments of the invention encompass methods of classifying an adult patient with septic shock as high risk or low risk, the method including: identifying an adult patient with septic shock; obtaining a sample from the patient; analyzing the sample to determine the level(s) of one or more biomarkers associated with septic shock in adult patients; determining whether the level(s) of the one or more biomarkers are elevated above a cut-off level, wherein the presence of an elevated level of one or more biomarkers associated with septic shock in adult patients indicates that the patient has an elevated likelihood of being classified as high risk and the absence of an elevated level of one or more biomarkers associated with septic shock in adult patients indicates that the patient has a reduced likelihood of being classified as high risk.

In some embodiments, the determination of whether the level(s) of the one or more biomarkers are elevated can be combined with one or more patient demographic data and/or clinical characteristics and/or results from other tests or indicia of septic shock. In some embodiments, the patient demographic data includes the age of the patient. In some embodiments, the patient demographic data and/or clinical characteristics and/or results from other tests or indicia of septic shock includes the septic shock causative organism, the presence or absence of chronic disease, and/or the gender, race, and/or co-morbidities of the patient.

In some embodiments, the one or more biomarkers can include CCL3, HSPA1B, IL8, CCL4, GZMB, and IL1A. In some embodiments, the one or more biomarkers can include CCL3, LCN2, HSPA1B, IL8, ELA2, MMP8, RETN, THBS, GZMB, ORM1, CCL4, LTF, IL1A, SULF2, and FGL2. In some embodiments, the one or more biomarkers can include the biomarkers listed in Table 1.

In some embodiments, the one or more biomarkers include all of CCL3, HSPA1B, IL8, CCL4, and GZMB. In some embodiments, a classification of high risk includes: a) an elevated level of CCL3 and a highly elevated level of IL8, or b) an elevated level of CCL3, a non-highly elevated level of IL8, and a highly elevated level of GZMB, or c) non-elevated levels of CCL3, HSPA1B, and CCL4, and an elevated level of lactate, or d) a non-elevated level of CCL3, elevated levels of HSPA1B and IL8, and a positive patient history of chronic disease, or e) non-elevated levels of CCL3, IL8, and GZMB, an elevated level of HSPA1B, and a positive patient history of chronic disease, or f) a non-elevated level of CCL3, an elevated level of HSPA1B, a highly elevated level of lactate, a negative patient history of chronic disease, and a patient age of older than 36 years, and a classification of low risk includes: g) non-elevated levels of CCL3, HSPA1B, and lactate, or h) non-elevated levels of CCL3 and HSPA1B, and elevated levels of lactate and CCL4, or i) non-elevated levels of CCL3 and IL8, elevated levels of HSPA1B and GZMB, and a positive patient history of chronic disease, or j) a non-elevated level of CCL3, an elevated level of HSPA1B, a negative patient history of chronic disease, and a patient age of 36 years or younger, or k) a non-elevated level of CCL3, a non-highly elevated level of lactate, an elevated level of HSPA1B, a negative patient history of chronic disease, and a patient age of over 36 years, or l) an elevated level of CCL3 and non-highly elevated levels of IL8 and GZMB. In some embodiments, a) an elevated level of CCL3 corresponds to a serum CCL3 concentration greater than 107 pg/ml, b) an elevated level of HSPA1B corresponds to a serum HSPA1B concentration greater than 112.966 ng/ml, c) an elevated level of IL8 corresponds to a serum IL8 concentration greater than 452 pg/ml, d) a highly elevated level of IL8 corresponds to a serum IL8 concentration greater than 4.012 ng/ml, e) an elevated level of GZMB corresponds to a serum GZMB concentration greater than 21 pg/ml, f) a highly elevated level of GZMB corresponds to a serum GZMB concentration greater than 25 pg/ml, g) an elevated level of lactate corresponds to a serum lactate concentration greater than 1.25 pg/ml, h) a highly elevated level of lactate corresponds to a serum lactate concentration greater than 1.35 pg/ml, and i) an elevated level of CCL4 corresponds to a serum CCL4 concentration greater than 48 pg/ml.

In some embodiments, the one or more biomarkers include all of CCL3, HSPA1B, IL8, CCL4, GZMB, and IL1A. In some embodiments, a classification of high risk includes: a) an elevated level of CCL3 and a highly elevated level of IL8, or b) elevated levels of CCL3 and GZMB, and a non-highly elevated level of IL8, or c) non-elevated levels of CCL3, HSPA1B, and CCL4, and a highly elevated level of lactate, or d) non-elevated levels of CCL3 and lactate, elevated levels of HSPA1B and IL8, and a positive patient history of chronic disease, or e) a non-elevated level of CCL3, elevated levels of HSPA1B and lactate, and a patient age of older than 44 years, or f) non-elevated levels of CCL3 and IL1A, elevated levels of HSPA1B and lactate, and a patient age of 44 years or younger, and a classification of low risk includes: g) non-elevated levels of CCL3 and HSPA1B, and a non-highly elevated level of lactate, or h) non-elevated levels of CCL3 and HSPA1B, an elevated level of CCL4, and a highly elevated level of lactate, or i) non-elevated levels of CCL3 and lactate, an elevated level of HSPA1B, and a negative patient history of chronic disease, or j) non-elevated levels of CCL3, lactate, and IL8, an elevated level of HSPA1B, and a positive patient history of chronic disease, or k) a non-elevated level of CCL3, elevated levels of HSPA1B, lactate, and IL1A, and a patient age of 44 years or younger, or l) a non-elevated level of GZMB, an elevated level of CCL3, and a non-highly elevated level of IL8. In some embodiments, a) an elevated level of CCL3 corresponds to a serum CCL3 concentration greater than 107 pg/ml, b) an elevated level of HSPA1B corresponds to a serum HSPA1B concentration greater than 113.000 ng/ml, c) an elevated level of IL8 corresponds to a serum IL8 concentration greater than 318 pg/ml, d) a highly elevated level of IL8 corresponds to a serum IL8 concentration greater than 4.000 ng·ml, e) an elevated level of GZMB corresponds to a serum GZMB concentration greater than 21 pg/ml, f) an elevated level of lactate corresponds to a serum lactate concentration greater than 1.35 pg/ml, g) a highly elevated level of lactate corresponds to a serum lactate concentration greater than 1.45 pg/ml, h) an elevated level of CCL4 corresponds to a serum CCL4 concentration greater than 48 ng/ml, and i) an elevated level of IL1A corresponds to a serum IL1A concentration greater than 0.8 pg/ml.

In some embodiments, the determination of whether the level(s) of the one or more biomarkers are elevated above a cut-off level includes applying the patient to a decision tree including the one or more biomarkers. The method of claim 14, wherein the patient can be applied to the decision tree depicted in FIG. 1, with terminal nodes 2, 4, 6, 9, 11, and 12 corresponding to a classification of high risk and terminal nodes 1, 3, 5, 7, 8, and 10 corresponding to a classification of low risk. The method of claim 14, wherein the patient can be applied to the decision tree depicted in FIG. 4, with terminal nodes 2, 5, 7, 9, 11, and 12 corresponding to a classification of high risk and terminal nodes 1, 3, 4, 6, 8, and 10 corresponding to a classification of low risk.

In some embodiments, the determination of whether the level(s) of the one or more biomarkers are elevated can be combined with one or more additional population-based risk scores. In some embodiments, the one or more population-based risk scores includes APACHE and/or SOFA.

In some embodiments, the sample can be obtained within the first hour of presentation with septic shock. In some embodiments, the sample can be obtained within the first 8 hours of presentation with septic shock. In some embodiments, the sample can be obtained within the first 24 hours of presentation with septic shock. In some embodiments, the sample can be obtained within the first 48 hours of presentation with septic shock.

Embodiments of the invention also encompass methods of providing individualized treatment for an adult patient with septic shock, wherein a patient classified as high risk via the methods described herein can be selected for one or more high risk therapies, and wherein a patient classified as low risk via the methods described herein can be excluded from one or more high risk therapies. In some embodiments, the one or more high risk therapies include extracorporeal membrane oxygenation/life support, plasmapheresis, pulmonary artery catheterization, and/or high volume continuous hemofiltration. In some embodiments, an outcome in can be improved an adult patient with septic shock, wherein a patient classified as high risk via the methods described herein can be selected for one or more high risk therapies, and wherein a patient classified as low risk via the methods described herein can be excluded from one or more high risk therapies.

Embodiments of the invention also encompass methods of selecting an adult patient with septic shock for a clinical trial, wherein a patient classified as high risk via the method of claim 1 can be selected for a moderate or high risk clinical trial, and wherein a patient classified as low risk via the methods described herein can be excluded from a moderate or high risk clinical trial.

Embodiments of the invention also include methods of predicting illness severity in an adult patient with septic shock, the method including: identifying an adult patient with septic shock; obtaining a sample from the patient; analyzing the sample to determine the level(s) of one or more biomarkers associated with septic shock in adult patients; determining whether the level(s) of the one or more biomarkers are elevated, wherein the presence of an elevated level of one or more biomarkers associated with septic shock in adult patients indicates that the patient has a severe case of septic shock and the absence of an elevated level of one or more biomarkers associated with septic shock in adult patients indicates that the patient has relatively less severe case of septic shock.

Embodiments of the invention also encompass diagnostic kits, tests, or arrays, including materials for quantification of at least two analytes, wherein the at least two analytes are biomarkers associated with septic shock in adult patients, an mRNA corresponding to any member of the group or its receptor, or any combinations thereof. In some embodiments, the at least two analytes can include CCL3, HSPA1B, IL8, CCL4, GZMB, and IL1A. In some embodiments, the at least two analytes include all of CCL3, HSPA1B, IL8, CCL4, and GZMB. In some embodiments, the at least two analytes include all of CCL3, HSPA1B, IL8, CCL4, GZMB, and IL1A. In some embodiments, the at least two analytes can include CCL3, LCN2, HSPA1B, IL8, ELA2, MMP8, RETN, THBS, GZMB, ORM1, CCL4, LTF, IL1A, SULF2, and FGL2. In some embodiments, the at least two analytes can include the biomarkers listed in Table 1.

In some embodiments, the diagnostic kit, test, or array includes a gene chip. In some embodiments, the gene chip includes a low density array. In some embodiments, the diagnostic kit, test, or array includes a surface with a DNA array.

BRIEF DESCRIPTION OF THE DRAWINGS

Those of skill in the art will understand that the drawings, described below, are for illustrative purposes only. The drawings are not intended to limit the scope of the present teachings in any way.

The root node provides the total number of patients in the derivation cohort and the number of survivors and non-survivors, with the respective rates. Each daughter node provides the respective decision rule criterion, and the number of survivors and non-survivors with the respective rates. The numbers above daughter nodes designate terminal nodes. Terminal nodes 1, 3, 5, 7, 8, and 10 are considered low risk nodes, whereas terminal nodes 2, 4, 6, 9, 11, and 12 are considered high risk terminal nodes. To calculate the diagnostic test characteristics, all subjects in the low risk terminal nodes (n=138) were classified as predicted survivors, whereas all subjects in the high risk terminal nodes (n=203) were classified as predicted non-survivors.

Figure 1:
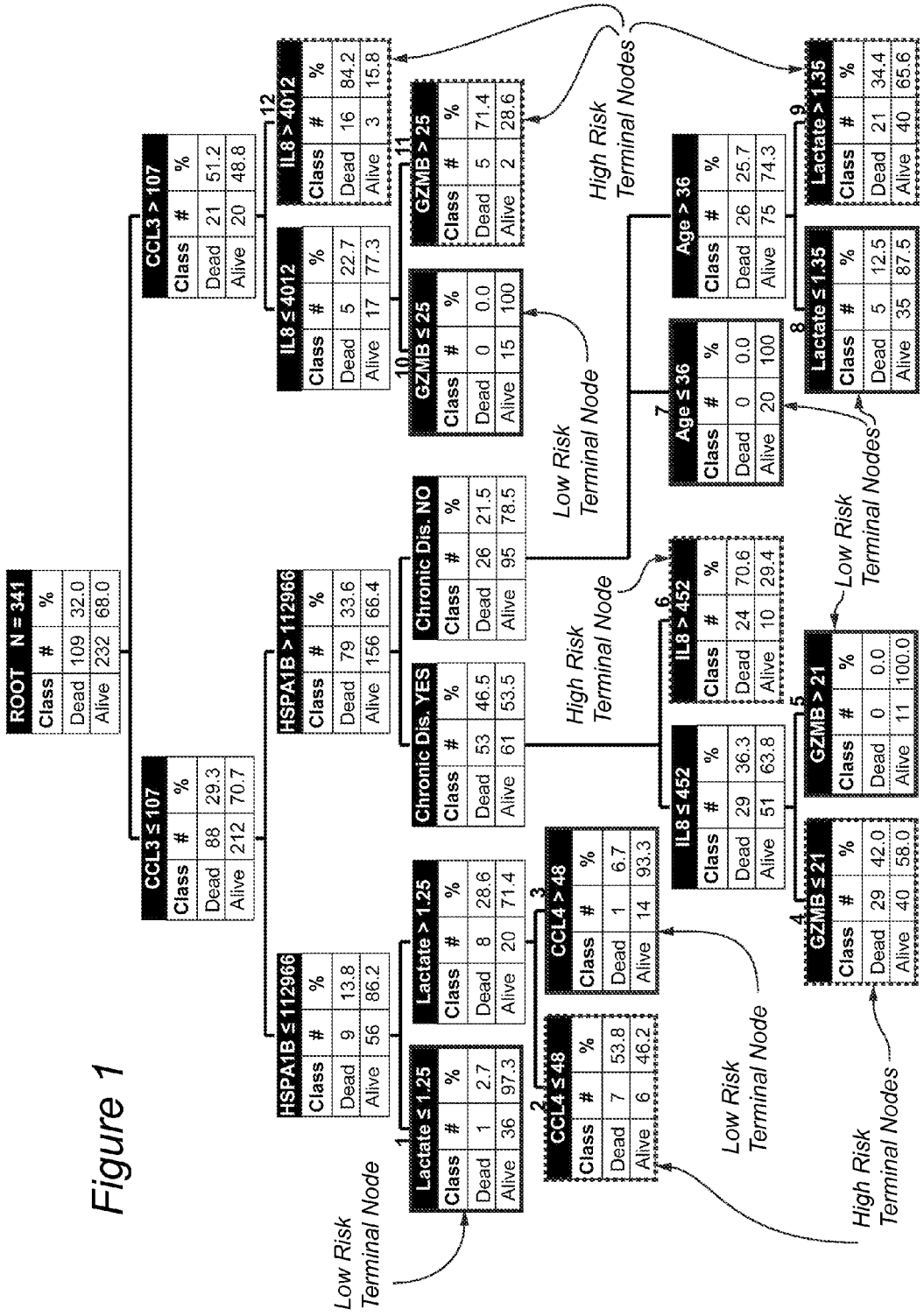
FIG. 1 depicts the classification tree from the derivation cohort (N=341). The classification tree consists of 11 decision rules and 22 daughter nodes and includes 5 of the 12 candidate stratification biomarkers, namely C-C chemokine ligand 3 (CCL3), heat shock protein 70 kDa 1B (HSPA1B), interleukin-8 (IL8), granzyme B (GZMB), and C-C chemokine ligand 4 (CCL4). For consistency, the serum concentrations of all candidate stratification biomarkers are provided in pg/ml. The classification tree also includes serum lactate concentrations (mmol/L), age, and the presence/absence of chronic disease.
Figure 2:
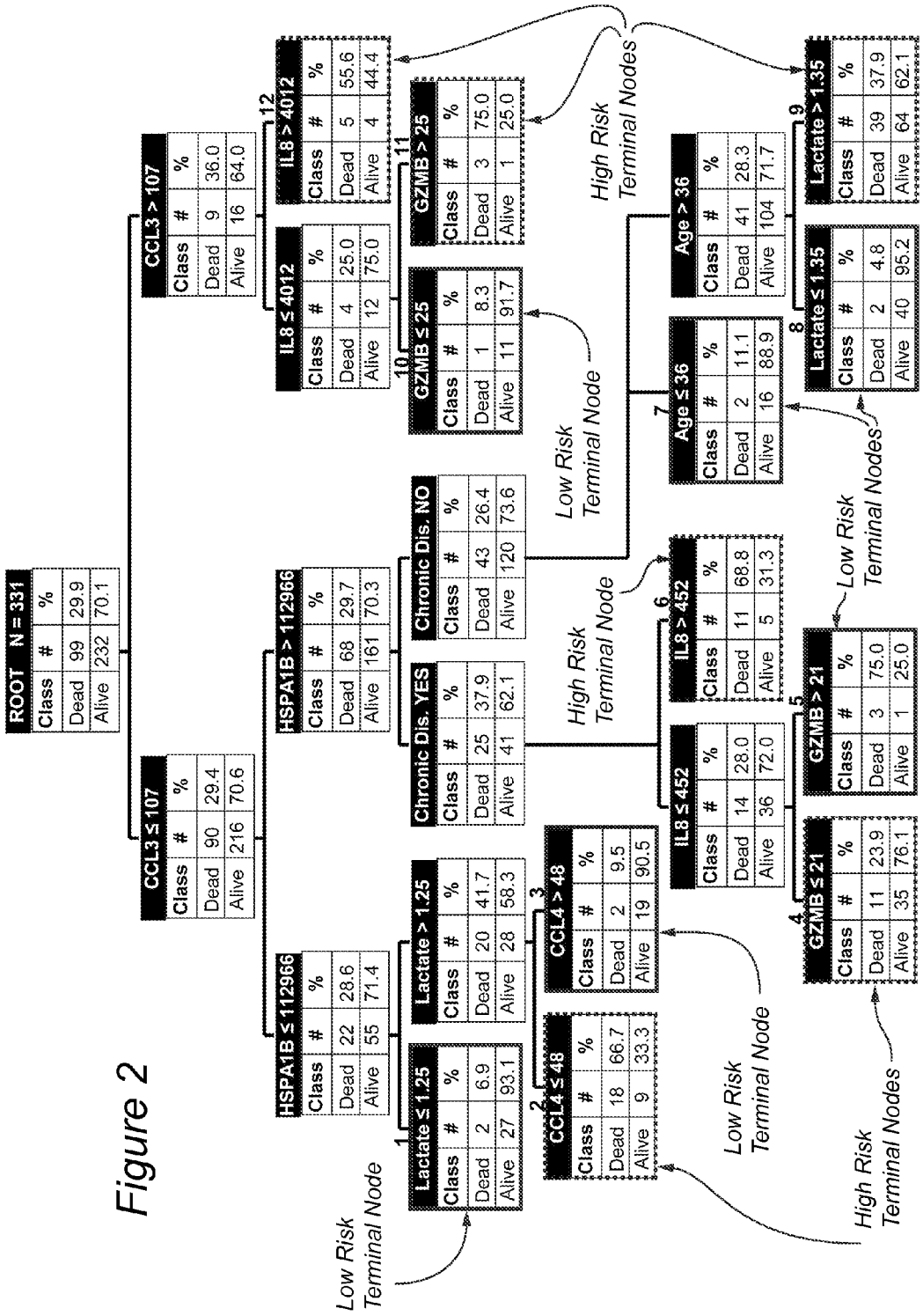

FIG. 2 depicts the classification tree for test cohort 1 (n=331). The decision rules from the derivation cohort tree (FIG. 1) were applied to test cohort 1 with no modifications. The same conventions that were applied to the derivation cohort for calculating diagnostic test characteristics are applied to test cohort 1.

Figure 3:
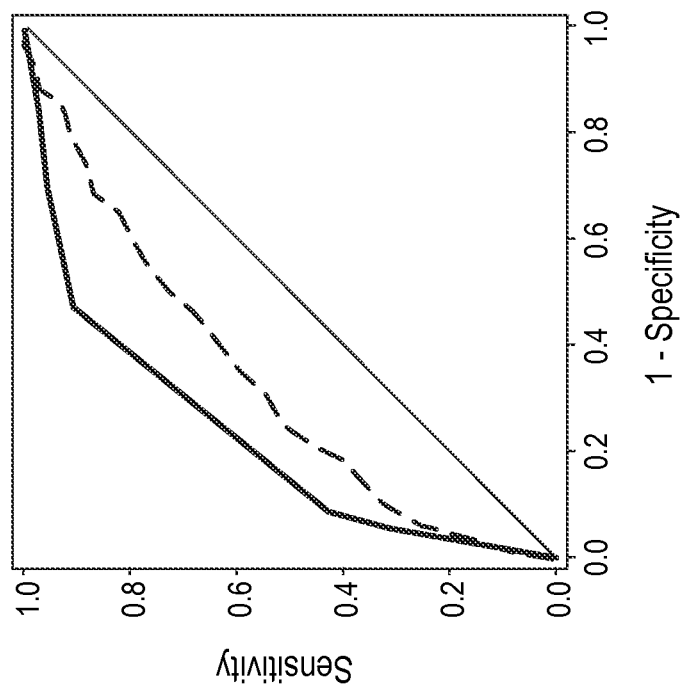

FIG. 3 depicts a comparison of receiver operating characteristic (ROC) curves for the biomarker-based model and the Acute Physiology and Chronic Health Evaluation II (APACHE II) system. The ROC curves were calculated based on the respective mortality probabilities and 28-day all-cause mortality and were based on all subjects in the combined derivation cohort and test cohort 1 (n=672). The ROC curve for the biomarker-based model (solid line) yielded an area under the curve (AUC) of 0.784 (0.747-0.820), whereas the ROC curve for APACHE II (dashed line) yielded an AUC of 0.676 (0.632-0.721). The AUCs were compared using the method of Hanley and McNeil to take into account the lack of independence between the two different methods (Hanley, et al. *Radiology* 148:839-43 (1983)). P=0.0001, biomarker-based model AUC vs. APACHE II AUC.

Figure 4:
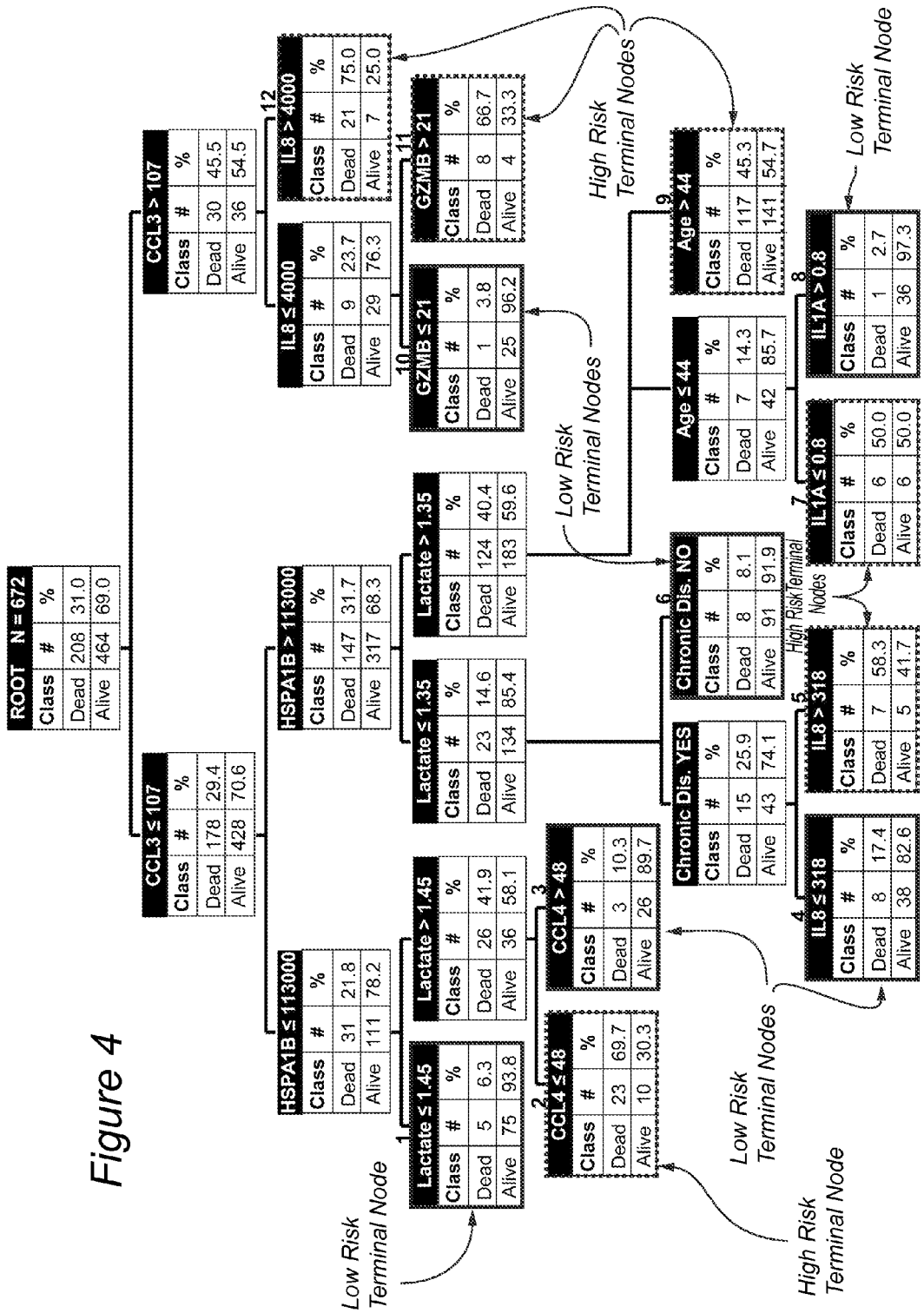

FIG. 4 depicts the calibrated classification tree based on all subjects in the derivation cohort and test cohort 1 (n=672). The classification tree consists of 11 decision rules and 22 daughter nodes. The classification tree includes 6 of the 12 candidate stratification biomarkers, namely C-C chemokine ligand 3 (CCL3), heat shock protein 70 kDa 1B (HSPA1B), interleukin-8 (IL8), granzyme B (GZMB), C-C chemokine ligand 4 (CCL4), and interleukin-1α (IL1A). The classification tree also includes serum lactate concentrations (mmol/L), age, and the presence/absence of chronic disease.

The conventions of the calibrated classification tree are the same as that described for FIG. 1. Terminal nodes 1, 3, 4, 6, 8, and 10 are considered low risk nodes, whereas terminal nodes 2, 5, 7, 9, 11, and 12 are considered high risk terminal nodes. To calculate the diagnostic test characteristics, all subjects in the low risk terminal nodes (n=317) were classified as predicted survivors, whereas all subjects in the high risk terminal nodes (n=355) were classified as predicted non-survivors.

Figure 5:
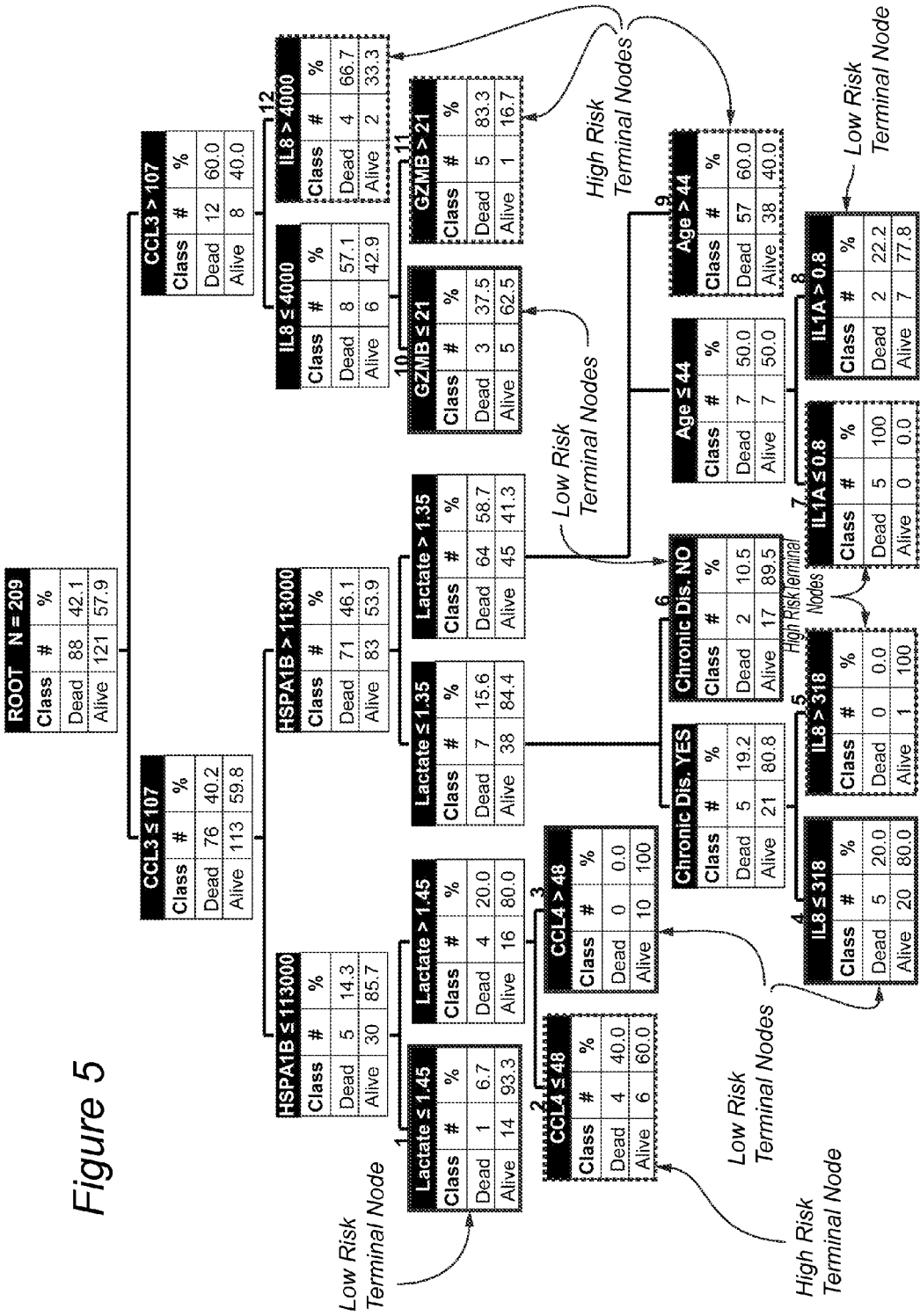

FIG. 5 depicts the classification tree for test cohort 2 (n=209). The decision rules from the calibrated classification tree (FIG. 4) were applied to test cohort 2 with no modifications. The same conventions that were applied to the derivation cohort for calculating diagnostic test characteristics were applied to the test cohort.

DETAILED DESCRIPTION OF THE INVENTION

Unless otherwise noted, terms are to be understood according to conventional usage by those of ordinary skill in the relevant art.

As used herein, the term "sample" encompasses a sample obtained from a subject or patient. The sample can be of any biological tissue or fluid. Such samples include, but are not limited to, sputum, saliva, buccal sample, oral sample, blood, serum, mucus, plasma, urine, blood cells (e.g., white cells), circulating cells (e.g. stem cells or endothelial cells in the blood), tissue, core or fine needle biopsy samples, cell-containing body fluids, free floating nucleic acids, urine, stool, peritoneal fluid, and pleural fluid, liquor cerebrospinalis, tear fluid, or cells therefrom. Samples can also include sections of tissues such as frozen or fixed sections taken for histological purposes or microdissected cells or extracellular parts thereof. A sample to be analyzed can be tissue material from a tissue biopsy obtained by aspiration or punch, excision or by any other surgical method leading to biopsy or resected cellular material. Such a sample can comprise cells obtained from a subject or patient. In some embodiments, the sample is a body fluid that include, for example, blood fluids, serum, mucus, plasma, lymph, ascitic fluids, gynecological fluids, or urine but not limited to these fluids. In some embodiments, the sample can be a non-invasive sample, such as, for example, a saline swish, a buccal scrape, a buccal swab, and the like.

As used herein, "blood" can include, for example, plasma, serum, whole blood, blood lysates, and the like.

As used herein, the term "assessing" includes any form of measurement, and includes determining if an element is present or not. The terms "determining," "measuring," "evaluating," "assessing" and "assaying" can be used interchangeably and can include quantitative and/or qualitative determinations.

As used herein, the term "diagnosing or monitoring" with reference to septic shock refers to a method or process of determining if a subject has or does not have septic shock or determining the severity or degree of septic shock.

As used herein, "outcome" can refer to the primary outcome studied, typically 28-day survival/mortality. The importance of survival/mortality in the context of adult septic shock is readily evident. The common choice of 28 days was based on the fact that 28-day mortality is a standard primary endpoint for interventional clinical trials involving critically ill patients.

As used herein, the terms "predicting outcome" and "outcome risk stratification" with reference to septic shock refers to a method or process of prognosing a patient's risk of a certain outcome. In some embodiments, predicting an outcome relates to determining a relative risk of mortality, or mortality probability. Such mortality risk can be high risk, moderate risk, moderate-high risk, moderate-low risk, or low risk. Alternatively, such mortality risk can be described simply as high risk or low risk, corresponding to high risk of death or high likelihood of survival, respectively. As related to the terminal nodes of the decision trees described herein, a "high risk terminal node" corresponds to a high mortality probability, whereas a "low risk terminal node" corresponds to a low mortality probability.

As used herein, the term "high risk clinical trial" refers to one in which the test agent has "more than minimal risk" (as defined by the terminology used by institutional review boards, or IRBs). In some embodiments, a high risk clinical trial is a drug trial.

As used herein, the term "low risk clinical trial" refers to one in which the test agent has "minimal risk" (as defined by the terminology used by IRBs). In some embodiments, a low risk clinical trial is one that is not a drug trial. In some embodiments, a low risk clinical trial is one that that involves the use of a monitor or clinical practice process. In some embodiments, a low risk clinical trial is an observational clinical trial.

As used herein, the terms "modulated" or "modulation," or "regulated" or "regulation" and "differentially regulated" can refer to both up regulation (i.e., activation or stimulation, e.g., by agonizing or potentiating) and down regulation (i.e., inhibition or suppression, e.g., by antagonizing, decreasing or inhibiting), unless otherwise specified or clear from the context of a specific usage.

As used herein, the term "subject" refers to any member of the animal kingdom. In some embodiments, a subject is a human patient. In some embodiments, a subject is an adult patient. In some embodiments, a pediatric patient is a patient under 18 years of age, while an adult patient is a patient 18 years of age or older.

As used herein, the terms "treatment," "treating," "treat," and the like, refer to obtaining a desired pharmacologic and/or physiologic effect. The effect can be prophylactic in terms of completely or partially preventing a disease or symptom thereof and/or can be therapeutic in terms of a partial or complete cure for a disease and/or adverse effect attributable to the disease. "Treatment," as used herein, covers any treatment of a disease in a subject, particularly in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease and/or relieving one or more disease symptoms. "Treatment" can also encompass delivery of an agent or administration of a therapy in order to provide for a pharmacologic effect, even in the absence of a disease or condition.

As used herein, the term "marker" or "biomarker" refers to a biological molecule, such as, for example, a nucleic acid, peptide, protein, hormone, and the like, whose presence or concentration can be detected and correlated with a known condition, such as a disease state. It can also be used to refer to a differentially expressed gene whose expression pattern can be utilized as part of a predictive, prognostic or diagnostic process in healthy conditions or a disease state, or which, alternatively, can be used in methods for identifying a useful treatment or prevention therapy.

As used herein, the term "expression levels" refers, for example, to a determined level of biomarker expression. The term "pattern of expression levels" refers to a determined level of biomarker expression compared either to a reference (e.g. a housekeeping gene or inversely regulated genes, or other reference biomarker) or to a computed average expression value (e.g. in DNA-chip analyses). A pattern is not limited to the comparison of two biomarkers but is more related to multiple comparisons of biomarkers to reference biomarkers or samples. A certain "pattern of expression levels" can also result and be determined by comparison and measurement of several biomarkers as disclosed herein and display the relative abundance of these transcripts to each other.

As used herein, a "reference pattern of expression levels" refers to any pattern of expression levels that can be used for the comparison to another pattern of expression levels. In some embodiments of the invention, a reference pattern of expression levels is, for example, an average pattern of expression levels observed in a group of healthy or diseased individuals, serving as a reference group.

As used herein, the term "decision tree" refers to a standard machine learning technique for multivariate data analysis and classification. Decision trees can be used to derive easily interpretable and intuitive rules for decision support systems.

Septic shock is a highly heterogeneous syndrome having variable expression in a given patient cohort. Dating from the 1990s, many clinical trials have been conducted to evaluate potential novel therapies for septic shock. With the exception of one therapy which now has FDA-approved specific labeling for septic shock in adults, namely activated protein C, virtually all of these trials have failed to demonstrate efficacy, despite being based on quality preclinical data (see, e.g., Sweeney, D. et al. *Intensive Care Med.* 37:666-88 (2009)). The above-mentioned activated protein C therapy, namely Xigris (Eli Lilly, Indianapolis, Ind.), has been taken off the market by the manufacturer because a large trial in Europe failed to demonstrate efficacy (see, e.g., Ranieri, V. et al. *N. Engl. J. Med.*, 366:2055-64 (2012)).

The reason for failure in clinical trials is presumably not because the biological/physiological principle being tested was fundamentally flawed. Rather, the primary reason for failure lies in the inability to effectively address the substantial heterogeneity that characterizes the syndrome of septic shock. Septic shock is a heterogeneous syndrome with the potential to negatively and directly affect all organ systems relevant to this challenge topic, including blood (coagulopathy), vascular (distributive shock), cardiac (cardiogenic shock), and respiratory (acute respiratory distress syndrome) function. The heterogeneity of septic shock has consistently challenged multiple investigators attempting to evaluate the efficacy of various experimental interventions.

A key challenge in the field is therefore to reduce and manage this heterogeneity by more effectively stratifying patients for the purposes of more rational and effective clinical research and clinical management. Heretofore, no effective way of stratifying adult patients who present with septic shock has been developed; an effective stratification process with some qualitative metric could inform decision-making and improve patient outcomes and prospective clinical trial design and management.

The concept of pre-intervention stratification in sepsis, and its positive impact on the efficacy of an experimental therapy, has been corroborated in a murine model of polymicrobial sepsis (Osuchowski, M. et al. *Crit. Care Med.* 37:1567-73 (2009)). While this study provides proof-of-concept, translating the concept to the bedside of critically ill patients remains a major challenge.

The ability to predict outcome, for individual patients and early in the course of illness, would be a major advancement in clinicians' ability to conduct septic shock interventional clinical trials in a more effective manner. Currently, there is no validated clinical tool that can achieve this important goal. While models that generate mortality prediction scores based on physiological variables, such as the Acute Physiology and Chronic Health Evaluation (APACHE), are very effective for estimating population-based outcome risks, these tools are not intended for stratification of individual patients.

A model was recently derived and tested that reliably predicts 28-day outcome in children (≤10 years of age) with septic shock (Wong, et al. *Crit. Care,* 16:R174 (2012)). A panel of serum/plasma protein biomarkers was considered for the model, with candidate biomarkers selected on the basis of extensive genome-wide expression studies (Kaplan, et al.

Ped. Crit. Care Med. 12:165-73 (2011)). The biomarker measurements represent the first 24 hours of admission to the intensive care unit (ICU), which is an optimal period for stratifying outcome risk because many important therapeutic decisions are made during this period. As described herein, the same candidate stratification biomarkers and approach was used to derive and test an analogous model in adults with septic shock.

Pediatric septic shock differs from adult septic shock in a variety of important aspects (Wynn, et al. *Pediatrics* 125: 1031-41 (2010); Cornell, et al. Pediatrics 125:1248-58 (2010)). Thus, from the standpoints of biology and physiology, the pediatric model is not directly applicable to adult populations. No robust, validated outcome risk stratification tool has heretofore been developed for septic shock in adults.

As described herein, a multi-biomarker-based outcome risk stratification model for adult septic shock that accurately predicts 28-day mortality has been derived and validated. This model reliably predicts outcome in adults with septic shock. The derivation and test cohorts used in the examples described herein were convenience samples obtained from the Vasopressin and Septic Shock Trial (VASST) database, which was compiled between July 2001 and April 2006 (Russell, et al. *N. Engl. J. Med.* 358:877-87 (2008)).

Twelve candidate serum protein stratification biomarkers were identified from previous genome-wide expression profiling. To derive the risk stratification tool, biomarkers were measured in plasma samples from 341 subjects with septic shock, obtained during the first 24 hours of admission to the intensive care unit. These results were used to generate a decision tree to predict 28-day outcome based on both biomarkers and clinical variables. The derived decision tree was subsequently validated in an independent cohort of 331 subjects with septic shock, calibrated using all subjects (n=672), and retested in another independent cohort (n=209).

A decision tree is a standard machine learning technique for multivariate data analysis and classification that can be used to derive easily interpretable and intuitive rules for decision support systems. Decision tress can be viewed as a recursive partitioning approach, in which data is hierarchically divided into strata by simple logical rules. The advantage of decision trees is their simplicity, ability to handle both categorical and numerical variables, as well as missing values, robustness to outliers and scaling, and the ability to combine feature selection with stratification and classification. As described herein, decision trees are used to select and combine the most predictive biomarkers with other input features into simple logical rules that can be used to classify patients and predict adverse effects, thereby enabling robust and accurate point-of-care prediction for septic shock in adult patients. Such knowledge allows for improved treatment protocols and outcomes.

The derived outcome risk stratification decision tree included a panel of biomarkers measured during the initial presentation to the ICU with septic shock, namely CCL3, HSPA1B, IL8, GZMB, and CCL4, in combination with admission lactate concentrations, age, and a derived variable describing the presence or absence of significant co-morbid conditions. A four step iterative process was used to derive the model, which was then tested in an independent cohort. Two cohorts were then pooled to calibrate the model, and the calibrated model was then re-tested in another independent cohort In the derivation cohort, sensitivity for mortality was 94% (95% CI 87-97), specificity was 56% (50-63), positive predictive value (PPV) was 50% (43-57), and negative predictive value (NPV) was 95% (89-98). Similar test characteristics were observed when the decision tree was applied to test cohort 1. The calibrated decision tree had the following test characteristics for mortality: the sensitivity was 88% (82-92), specificity was 63% (58-67), PPV was 51% (46-57), and NPV was 92% (88-94). Similar test characteristics were observed when the calibrated decision tree was applied to test cohort 2. The derived and tested risk multi-biomarker-based model that reliably stratifies adults with septic shock therefore can be used to enhance clinical decision making, to adjust for risk in clinical trials, and to serve as a septic shock-specific quality metric.

When applied to the two independent test cohorts, the test characteristics of the models were similar to those of in the derivation and calibration cohorts, respectively. For all subjects in the study (n=881), the high risk terminal nodes of the calibrated model identified a cohort with an overall mortality rate of 56%, whereas the low risk terminal nodes identified a cohort with an overall mortality rate of 11%. Thus, a basic, dichotomous interpretation of the model is the ability to segregate a heterogeneous cohort of patients with septic shock/severe sepsis into two broad groups having an approximately 5-fold difference in mortality risk. An alternative, non-dichotomous interpretation of the model is to view each terminal node individually, which provides a clinically relevant range of mortality probabilities having variable degrees of consistency.

A strength of the biomarker-based outcome risk stratification model described herein is the initial approach to deriving the candidate stratification biomarkers. Using an extensive genome-wide expression databank, 117 gene probes possibly associated with outcome in a cohort of children with septic shock were identified (Kaplan, et al. *Ped. Crit. Care Med.* 12:165-73 (2011); Cvijanovich, et al. *Physiol. Genomics* 34:127-34 (2008); Shanley, et al. *Mol. Med.* 13:495-508 (2007); Wong, et al. *Crit. Care Med.* 37:1558-66 (2009); Wong, et al. *BMC Med.* 7:34 (2009); Wong, et al. *Physiol. Genomics* 30:146-55 (2007)). From these 117 gene probes, 12 biomarkers were selected using a priori criteria, as described in Example 1.

The modeling process considered the candidate stratification biomarkers, as well as clinical variables having potential associations with outcome. The biomarkers dominated the upper level decision rules, whereas the clinical variables contributed to the lower level decision rules, or not at all. Thus, the biomarkers contribute independent new information that allows for an improved prognostic model. The NRI calculations further support this assertion. The pediatric modeling procedures yielded similar results (Wong, et al. *Crit. Care,* 16:R174 (2012)), with the upper level decision rules of the pediatric and adult models consisting of the same three biomarkers (CCL3, HSPA1B, and IL8), albeit with cutoff values that are specific to the respective populations. This suggests consistent utility for these three particular stratification biomarkers.

The decision rules that contribute to the model, as well as the predictive consistency of several terminal nodes across cohorts, may provide some biological information regarding the early host response during septic shock and its association with outcome, as well as the biological plausibility of the model. For example, occupying terminal 1 of the calibrated decision tree is associated with a consistently low mortality risk in both the calibration cohort (6.3% mortality risk) and test cohort 2 (6.7% mortality risk). Occupying terminal node 1 requires a combination of CCL3, HSPA1B, and lactate concentrations less than or equal to the respective decision rules. This indicates that patients with a relatively low level of inflammation (based on relatively low CCL3 and HSPA1B concentrations) and adequate tissue perfusion (based on relatively low lactate concentrations) are at low risk for mortality. Conversely, occupying terminal node 12 of the calibrated tree is associated with a consistently high mortality risk in both the calibration cohort (75.0% mortality risk) and test cohort 2 (66.7% mortality risk). Occupying terminal node 12 requires a combination of CCL3 and IL8 concentrations greater than the respective decision rules. Patients with an excessive degree of inflammation (based on relatively high CCL3 and IL8 concentrations) therefore can have a substantially increased risk of mortality. A similar association between excessive inflammation and increased risk of mortality is evident in terminal node 11, which is defined by a CCL3 concentration greater than the decision rule, an IL8 concentration less than or equal than the decision rule, followed by a GZMB concentration greater than the decision rule. The ability to partition the data in this way allows for not only improved decision making but also improved understanding of the complex interplay of pathologies resulting in mortality and, potentially, targets for therapeutic intervention.

The 2008 Surviving Sepsis Campaign International Guidelines for the Management of Severe Sepsis and Septic Shock recommend a serum lactate concentration >4 mmol/L as a threshold indicator of tissue hypoperfusion warranting initiation of protocolized, quantitative resuscitation (Dellinger, et al. Crit. Care Med., 36:296-327 (2008)). The 2012 guidelines provide the same recommendation based on a reported mortality of 46% in septic patients with both hypotension and serum lactate concentration >4 mmol/L (Dellinger, et al. Crit. Care Med., 41:580-637 (2012); Levy, et al. Crit. Care Med., 38:367-74 (2010)). In contrast, the calibrated decision tree described herein (FIG. 4) indicates that serum lactate concentrations in the upper range of normal (e.g. >1.35 mmol/L), in combination with other decision rules, are associated with increased risk of mortality. Consistent with this observation, two recent studies reported an association between lactate concentrations in the upper range of normal and increased mortality in patients with either septic shock or other forms of critical illness (Wacharasint, et al. Shock, 38:4-10 (2012); Nichol, et al. Crit. Care, 14:R25 (2010)). Also consistent with this observation are the recently revised definitions of sepsis and severe sepsis, which include a serum lactate concentration >1 mmol/L as a diagnostic criterion for sepsis, and a serum concentration "above upper limits of laboratory normal" as a diagnostic criterion for severe sepsis (Dellinger, et al. Crit. Care Med., 41:580-637 (2012)).

There has heretofore been no validated risk stratification tool for adult septic shock that performs as effectively as the biomarker-based model described herein. Physiology-based scoring systems are robust for predicting outcomes of general ICU populations but are not intended for stratification and tend to perform less well when applied to specific diseases or syndromes (Vincent, et al. Crit. Care Med. 38:283-7 (2010)). Nonetheless, it is useful to compare the effectiveness of the biomarker-based outcome risk stratification model with that of a physiology-based scoring system. The available data allowed a comparison of the biomarker-based model performance with both the commonly used Acute Physiology and Chronic Health Evaluation II (APACHE II) and III (APACHE III) systems for the classification of disease severity within the first 24 hours of ICU admission. The biomarker-based model was found to outperform APACHE II and III in these cohorts.

There were several important differences between the various cohorts used in the examples described herein. First, since the initial derivation cohort was derived from a database generated during an interventional clinical trial, it is likely that the subjects in the derivation cohort represent a more highly selected population of patients with septic shock, compared to the subjects in the test cohorts, who were derived from observational databases. Second, the study subjects represent three different health care systems, namely Canada, Finland, and the United States. Third, all of the subjects in the derivation cohort and test cohort 2 met criteria for septic shock, whereas the subjects in test cohort 1 met criteria for either septic shock (81.9%) or severe sepsis (19.1%). Fourth, there were significant differences between cohorts with respect to age, gender, illness severity, time to death, and chronic disease burden. The models performed well in two independent test cohorts, thus indicating that the model has generalizability and utility across a broad range of adults with septic shock/severe sepsis.

The biomarker-based adult sepsis outcome risk stratification model has a number of potential applications, including the ability to substantially enhance the conduct of future clinical trials, inform decision making for individual patients, and serve as a metric for quality improvement efforts. First, this model can enhance patient inclusion criteria and enrollment for interventional randomized, controlled trials. For example, the outcome risk stratification model can be used to exclude patients at the extreme upper and lower ranges of mortality risk, while simultaneously selecting those with intermediate mortality risks potentially more responsive to novel therapeutic interventions. This approach also can increase the ethicality of clinical trials, particularly if an experimental therapy carries more than minimal risk. Excluding the lowest risk patients who are likely to survive without experimental intervention reduces their risk of adverse effects of the new intervention, and excluding the highest risk patients unlikely to survive with any therapy removes patients who may be too sick to respond to treatment, all of which could enhance the potential absolute risk reduction of the new therapy for moderate risk patients. Outside of the clinical trial context, the model could, by more accurately prognosticating outcome, help to inform individual patient decision-making, help to inform allocation of ICU resources, and serve as a metric for quality improvement efforts.

In conclusion, a multi-biomarker-based risk model that demonstrates the ability to risk-stratify adults with septic shock has been derived and tested. Favorable comparisons to existing scoring systems and good performance in the context of potentially profound confounding factors support the generalizability and utility of the model. This model has the potential to substantially enhance the conduct of future clinical trials, inform decision making for individual patients, and serve as a metric for quality improvement efforts.

The multi-biomarker-based risk model can be periodically updated. As more patients are included into the modeling process, some of the biomarker cutoff values included in the decision trees depicted in FIGS. 1 and 4 can change. In addition, new biomarkers can be identified that can contribute to the decision tree, or the previously tested biomarkers might be useful for refining the risk stratification, or additional patient information can be incorporated into the decision tree or used in combination with the decision tree. Such changes can enhance predictive performance and further increase generalizability of the decision tree.

Certain embodiments of the invention include using quantification data from a gene-expression analysis and/or from an mRNA analysis, from a sample of blood, urine, saliva, or the like. Embodiments of the invention include not only methods of conducting and interpreting such tests but also include reagents, kits, assays, and the like, for conducting the tests.

In an exemplary embodiment, the outcome risk stratification method is carried out on a patient to predict an outcome for an adult patient with septic shock. A serum sample is obtained from an adult patient. Serum concentrations of CCL3, HSPA1B, IL8, GZMB, and CCL4 are then measured (e.g. using a magnetic bead multi-plex platform and a Luminex® 100/200 System). The results are then used in order to predict an outcome for an adult patient with septic shock.

In another exemplary embodiment, serum concentrations of CCL3, HSPA1B, IL8, GZMB, and CCL4 are measured (e.g. using a magnetic bead multi-plex platform and a Luminex® 100/200 System), as well as serum lactate concentration. The results from the serum concentrations of CCL3, HSPA1B, IL8, GZMB, and CCL4 and the serum lactate concentration are then used in combination in order to predict an outcome for an adult patient with septic shock.

In another exemplary embodiment, serum concentrations of CCL3, HSPA1B, IL8, GZMB, and CCL4 and serum lactate concentration are measured (e.g. using a magnetic bead multi-plex platform and a Luminex® 100/200 System), and the presence or absence of chronic disease is determined, defined as the presence or absence of at least one of the following co-morbidities: congestive heart failure (NYHA Class IV CHF), chronic obstructive pulmonary disease (COPD), requirement for chronic dialysis, chronic hepatic failure, requirement for chronic steroids, and hematologic or metastatic solid organ malignancy. The results from the serum concentrations of CCL3, HSPA1B, IL8, GZMB, and CCL4, serum lactate concentration, and the presence or absence of chronic disease are used in combination in order to predict an outcome for an adult patient with septic shock.

In another exemplary embodiment, serum concentrations of CCL3, HSPA1B, IL8, GZMB, and CCL4 and serum lactate concentration are measured (e.g. using a magnetic bead multi-plex platform and a Luminex® 100/200 System), the presence or absence of chronic disease is determined, and the patient's age is noted. The results from the serum concentrations of CCL3, HSPA1B, IL8, GZMB, and CCL4, serum lactate concentration, the presence or absence of chronic disease, and the patient's age are then used in combination in order to predict an outcome for an adult patient with septic shock.

In another exemplary embodiment, the outcome risk stratification method is carried out on a patient to predict an outcome for an adult patient with septic shock. A serum sample is obtained from an adult patient. Serum concentrations of CCL3, HSPA1B, IL8, GZMB, CCL4, and IL1A are then measured (e.g. using a magnetic bead multi-plex platform and a Luminex® 100/200 System). The results are then used in order to predict an outcome for an adult patient with septic shock.

In another exemplary embodiment, serum concentrations of CCL3, HSPA1B, IL8, GZMB, CCL4, and IL1A are measured (e.g. using a magnetic bead multi-plex platform and a Luminex® 100/200 System), as well as serum lactate concentration. The results from the serum concentrations of CCL3, HSPA1B, IL8, GZMB, and CCL4 and the serum lactate concentration are then used in combination in order to predict an outcome for an adult patient with septic shock.

In another exemplary embodiment, serum concentrations of CCL3, HSPA1B, IL8, GZMB, CCL4, and IL1A and serum lactate concentration are measured (e.g. using a magnetic bead multi-plex platform and a Luminex® 100/200 System), and the presence or absence of chronic disease is determined. The results from the serum concentrations of CCL3, HSPA1B, IL8, GZMB, CCL4, and IL1A, serum lactate concentration, and the presence or absence of chronic disease are then used in combination in order to predict an outcome for an adult patient with septic shock.

In another exemplary embodiment, serum concentrations of CCL3, HSPA1B, IL8, GZMB, CCL4, and IL1A and serum lactate concentration are measured (e.g. using a magnetic bead multi-plex platform and a Luminex® 100/200 System), the presence or absence of chronic disease is determined, and the patient's age is noted. The results from the serum concentrations of CCL3, HSPA1B, IL8, GZMB, CCL4, and IL1A, serum lactate concentration, the presence or absence of chronic disease, and the patient's age are then used in combination in order to predict an outcome for an adult patient with septic shock.

Use of the decision tree depicted in FIG. 1 in order to predict an outcome for an adult patient with septic shock is another exemplary embodiment of the invention. Use of the decision tree depicted in FIG. 4 in order to predict an outcome for an adult patient with septic shock is another exemplary embodiment of the invention.

In some embodiments, an adult patient with septic shock evaluated via the outcome risk stratification method described herein by subjecting the patient to the decision tree depicted in FIG. 1 or FIG. 4. In some embodiments, a patient that ends up in one of the low risk terminal nodes of the decision tree is determined to have a mortality probability ranging from 0% to 18%. In some embodiments, a patient that ends up in one of the low risk terminal nodes of the decision tree is determined to have a mortality probability of 0%, 1%, 2%, 3%, 4%, 5%, 6%, 7%, 8%, 9%, 10%, 11%, 12%, 13%, 14%, 15%, 16%, or 17%. In some embodiments, a patient that ends up in one of the high risk nodes of the decision tree is determined to have a mortality probability ranging from 18% to 40%. In some embodiments, a patient that ends up in one of the low risk terminal nodes of the decision tree is determined to have a mortality probability of 18%, 19%, 20%, 21%, 22%, 23%, 24%, 25%, 26%, 27%, 28%, 29%, 30%, 31%, 32%, 33%, 34%, 35%, 36%, 37%, 38%, or 39%. In some embodiments, a patient that ends up in one of the high risk nodes of the decision tree is determined to have a mortality probability ranging from 40% to 100%. In some embodiments, a patient that ends up in one of the low risk terminal nodes of the decision tree is determined to have a mortality probability of 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%. In some embodiments, any patient that is not considered to be low risk can be classified as high risk, i.e. a patient that is considered be to moderate risk or moderate-high risk can be classified as high risk.

Sample Acquisition

Stratification of patients presenting with septic shock becomes increasingly difficult as time progresses due to the inherently acute symptoms of septic shock. Accordingly, the methods described herein which allow for stratification of individual adult patients in order to determine the patient's outcome risk involve acquiring a sample from an adult patient early in the patient's course of diagnosis and treatment.

In some embodiments, a sample is acquired from an adult patient within the first 60 minutes of presentation with septic shock. In some embodiments, a sample is acquired from an adult patient within the first 8 hours of presentation with septic shock. In some embodiments, a sample is acquired from an adult patient within the first 24 hours of presentation with septic shock. In some embodiments, a sample is acquired from an adult patient within the first 48 hours of presentation with septic shock. In some embodiments, a sample is acquired from an adult patient within the first 72 hours of presentation with septic shock.

In some embodiments, a sample is acquired from an adult patient within the first 1, 2, 3, 4, 5, 6, 7, 8, 9, or 10 hours of presentation with septic shock. In some embodiments, a sample is acquired from an adult patient within the first 11, 12, 13, 14, 15, 16, 17, 18, 19, or 20 hours of presentation with septic shock. In some embodiments, a sample is acquired from an adult patient within the first 21, 22, 23, 24, 25, 26, 27, 28, 29, or 30 hours of presentation with septic shock. In some embodiments, a sample is acquired from an adult patient within the first 31, 32, 33, 34, 35, 36, 37, 38, 39, or 40 hours of presentation with septic shock. In some embodiments, a sample is acquired from an adult patient within the first 41, 42, 43, 44, 45, 46, 47, 48, 49, or 50 hours of presentation with septic shock. In some embodiments, a sample is acquired from an adult patient within the first 51, 52, 53, 54, 55, 56, 57, 58, 59, or 60 hours of presentation with septic shock. In some embodiments, a sample is acquired from an adult patient within the first 61, 62, 63, 64, 65, 66, 67, 68, 69, or 70 hours of presentation with septic shock. In some embodiments, a sample is acquired from an adult patient within the first 71, 72, 73, 74, 75, 76, 77, 78, 79, or 80 hours of presentation with septic shock.

Additional Patient Information

The demographic data, clinical characteristics, and/or results from other tests or indicia of septic shock specific to an adult patient with septic shock can affect the patient's outcome risk. Accordingly, such demographic data, clinical characteristics, and/or results from other tests or indicia of septic shock can be incorporated into the methods described herein which allow for stratification of individual adult patients in order to determine the patient's outcome risk. Such demographic data, clinical characteristics, and/or results from other tests or indicia of septic shock can also be used in combination with the methods described herein which allow for stratification of individual patients in order to determine the patient's outcome risk.

Such patient demographic data can include, for example, the patient's age, race, gender, and the like.

In some embodiments, the biomarker-based risk stratification model described herein can incorporate the patient's age to determine an outcome risk. In some embodiments, the biomarker-based risk stratification model described herein can incorporate the patient's race to determine an outcome risk. In some embodiments, the biomarker-based risk stratification model described herein can incorporate the patient's gender to determine an outcome risk.

In some embodiments, the biomarker-based risk stratification model described herein can be used in combination with the patient's age to determine an outcome risk. In some embodiments, the biomarker-based risk stratification model described herein can be used in combination with the patient's race to determine an outcome risk. In some embodiments, the biomarker-based risk stratification model described herein can be used in combination with the patient's gender to determine an outcome risk.

Such patient clinical characteristics and/or results from other tests or indicia of septic shock can include, for example, the patient's co-mobidities and/or septic shock causative organism, and the like.

Patient co-morbidities can include, for example, acute lymphocytic leukemia, acute myeloid leukemia, aplastic anemia, atrial and ventricular septal defects, bone marrow transplantation, caustic ingestion, chronic granulomatous disease, chronic hepatic failure, chronic lung disease, chronic lymphopenia, chronic obstructive pulmonary disease (COPD), congestive heart failure (NYHA Class IV CHF), Cri du Chat syndrome, cyclic neutropenia, developmental delay, diabetes, DiGeorge syndrome, Down syndrome, drowning, end stage renal disease, glycogen storage disease type 1, hematologic or metastatic solid organ malignancy, hemophagocytic lymphohistiocytosis, hepatoblastoma, heterotaxy, hydrocephalus, hypoplastic left heart syndrome, IPEX Syndrome, kidney transplant, Langerhans cell histiocytosis, liver and bowel transplant, liver failure, liver transplant, medulloblastoma, metaleukodystrophy, mitochondrial disorder, multiple congenital anomalies, multi-visceral transplant, nephrotic syndrome, neuroblastoma, neuromuscular disorder, obstructed pulmonary veins, Pallister Killian syndrome, Prader-Willi syndrome, requirement for chronic dialysis, requirement for chronic steroids, retinoblastoma, rhabdomyosarcoma, rhabdosarcoma, sarcoma, seizure disorder, severe combined immune deficiency, short gut syndrome, sickle cell disease, sleep apnea, small bowel transplant, subglottic stenosis, tracheal stenosis, traumatic brain injury, trisomy 18, type 1 diabetes mellitus, unspecified brain tumor, unspecified congenital heart disease, unspecified leukemia, VATER Syndrom, Wilms tumor, and the like. Any one or more of the above patient co-morbidities can be indicative of the presence or absence of chronic disease in the patient.

Septic shock causative organisms can include, for example, *Acinetobacter baumannii*, Adenovirus, *Bacteroides* species, *Candida* species, *Capnotyophaga jenuni*, Cytomegalovirus, *Enterobacter cloacae, Enterococcus faecalis, Escherichia coli,* Herpes simplex virus, Human metapneumovirus, Influenza A, *Klebsiella pneumonia, Micrococcus* species, mixed bacterial infection, *Moraxella catarrhalis, Neisseria meningitides*, Parainfluenza, *Pseudomonas* species, *Serratia marcescens, Staphylococcus aureus, Streptococcus agalactiae, Streptococcus milleri, Streptococcus pneumonia, Streptococcus pyogenes*, unspecified gram negative rods, unspecified gram positive cocci, and the like.

In some embodiments, the biomarker-based risk stratification model described herein can incorporate the patient's co-morbidities to determine an outcome risk. In some embodiments, the biomarker-based risk stratification model described herein can incorporate the patient's septic shock causative organism to determine an outcome risk.

In some embodiments, the biomarker-based risk stratification model described herein can be used in combination with the patient's co-morbidities to determine an outcome risk. In some embodiments, the biomarker-based risk stratification model described herein can be used in combination with the patient's septic shock causative organism to determine an outcome risk.

Population-Based Risk Scores

A number of models that generate mortality prediction scores based on physiological variables have been developed to date. These can include the Sequential Organ Failure Assessment (SOFA) and APACHE models, and the like. The APACHE model considered can be APACHE I, APACHE II, APACHE III, APACHE IV, or a subsequent iteration of APACHE.

Such models can be very effective for estimating population-based outcome risks but are not intended for stratification of individual patients. The methods described herein which allow for stratification of individual patients can be used alone or in combination with one or more existing population-based risk scores.

In some embodiments, the biomarker-based risk stratification model described herein can be used with one or more additional population-based risk scores. In some embodiments, the biomarker-based risk stratification model described herein can be used in combination with APACHE. In some embodiments, the biomarker-based risk stratification model described herein can be used in combination with a population-based risk score other than APACHE.

High Risk Therapies

High risk, invasive therapeutic and support modalities can be used to treat septic shock. The methods described herein which allow for stratification of individual adult patients in order to determine the patient's outcome risk can help inform clinical decisions regarding the application of high risk therapies to specific adult patients, based on the patient's outcome risk.

High risk therapies include, for example, extracorporeal membrane oxygenation/life support, plasmapheresis, pulmonary artery catheterization, high volume continuous hemofiltration, and the like.

In some embodiments, individualized treatment can be provided to an adult patient by selecting a adult patient classified as high risk by the methods described herein for one or more high risk therapies. In some embodiments, individualized treatment can be provided to an adult patient by excluding an adult patient classified as low risk from one or more high risk therapies.

Certain embodiments of the invention include using quantification data from a gene-expression analysis and/or from a mRNA analysis, from a sample of blood, urine, saliva, broncho-alveolar lavage fluid, or the like. Embodiments of the invention include not only methods of conducting and interpreting such tests but also include reagents, kits, assays, and the like, for conducting the tests.

Prognostic determination can be described by evaluating control groups to obtain four critical test characteristics, namely positive predictive value (PPV), negative predictive value (NPV), sensitivity, and specificity, which provide information regarding the effectiveness of the test. The PPV of a particular prognostic method represents the proportion of subjects with a positive test result who are correctly prognosed; for tests with a high PPV, a positive test indicates the presence of the condition in question. The NPV of a particular prognostic method represents the proportion of subjects with a negative test result who are correctly prognosed; for tests with a high NPV, a negative test indicates the absence of the condition in question. Sensitivity represents the proportion of correctly identified subjects who are actual positives; for tests with high sensitivity, a positive test indicates the presence of the condition in question. Specificity represents the proportion of correctly identified subjects who are actual negatives; for tests with high specificity, a negative test indicates the absence of the condition in question.

The threshold for the disease state can alternatively be defined as a 1-D quantitative score, or diagnostic cutoff, based upon receiver operating characteristic (ROC) analysis. The quantitative score based upon ROC analysis can be used to determine the specificity and/or the sensitivity of a given diagnosis based upon subjecting a patient to the decision tree described herein in order to predict an outcome for an adult patient with septic shock.

The correlations disclosed herein, between septic shock biomarker levels and/or mRNA levels and/or gene expression levels, provide a basis for predicting an outcome for an adult patient with septic shock, or for conducting a stratification of patients with septic shock, or for enhancing the reliability of a prediction of an outcome for an adult patient with septic shock by combining the results of a quantification of a septic shock biomarker with results from other tests or indicia of septic shock. For example, the results of a quantification of one biomarker could be combined with the results of a quantification of one or more additional biomarker, cytokine, mRNA, or the like. Thus, even in situations in which a given biomarker correlates only moderately or weakly with septic shock or with a septic shock outcome prediction, providing only a relatively small PPV, NPV, specificity, and/or sensitivity, the correlation can be one indicium, combinable with one or more others that, in combination, provide an enhanced clarity and certainty of predictive outcome. Accordingly, the methods and materials of the invention are expressly contemplated to be used both alone and in combination with other tests and indicia, whether quantitative or qualitative in nature.

Having described the invention in detail, it will be apparent that modifications, variations, and equivalent embodiments are possible without departing the scope of the invention defined in the appended claims. Furthermore, it should be appreciated that all examples in the present disclosure are provided as non-limiting examples.

EXAMPLES

The following non-limiting examples are provided to further illustrate embodiments of the invention disclosed herein. It should be appreciated by those of skill in the art that the techniques disclosed in the examples that follow represent approaches that have been found to function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention.

Example 1

Patient Stratification

Study Subjects and Plasma Samples for the Derivation Cohort

The derivation cohort study subjects (n=341) were obtained from an existing database generated during the Vasopressin and Septic Shock Trial (VASST), a randomized, concealed, norepinephrine-controlled trial testing the efficacy of low-dose vasopressin versus norepinephrine in adult patients with septic shock (Current Controlled Trials No. ISRCTN9485869). The original VASST publication describes all protocol details (Russell, et al. *N. Engl. J. Med.* 358:877-87 (2008)). The original informed consent form for VASST allows for secondary analyses of clinical data and biological samples.

Study Subjects and Plasma Samples for Independent Test Cohort 1:

The independent test cohort 1 study subjects (n=331) were pooled from two sources. Of the subjects, 243 were derived from the FINNSEPSIS database, a prospective, observational, multi-center cohort study of incidence and outcome of severe sepsis/septic shock in Finland, as previously described (Karlsson, et al. *Intensive Care Medicine*, 33:435-43 (2007)). An additional 88 subjects were derived from a single center, observational database at St. Paul's Hospital in Vancouver, British Columbia, as previously described (Nakada, et al. *Am. J. Resp. Crit. Care Med.*, 181:14309 (2010)). The consent forms for both observational studies allow for the secondary analyses of clinical data and biological samples.

Study Subjects and Plasma Samples for Independent Test Cohort 2:

The independent test cohort 2 study subjects (n=209) were obtained from the Molecular Epidemiology of Severe Sepsis in the Intensive Care Unit (MESSI) study, an ongoing cohort study at the Hospital of the University of Pennsylvania, Philadelphia, Pa. After informed consent, eligible patients were enrolled in either the emergency department or the medical intensive care unit of the Hospital of the University of Pennsylvania. Septic shock was defined using published criteria (Levy, et al. *Crit. Care Med.*, 31:1250-6 (2003)). Plasma samples were collected in citrated vacutainers, centrifuged within 30 minutes, and subsequently frozen at −80° C.

Candidate Stratification Biomarkers

A panel of 117 gene probes (Table 1) has been previously shown to have predictive strength for poor outcomes in microarray-based studies involving children with septic shock (Kaplan, et al. *Ped. Crit. Care Med.* 12:165-73 (2011)). These candidate biomarker gene probes were found to be common to gene lists developed through both a statistics-based approach and a class prediction-based approach.

TABLE 1

List of 117 candidate biomarker gene probes.

| Affymetrix ID | Gene Symbol | Description |
| --- | --- | --- |
| 222608_s_at | ANLN | anillin, actin binding protein |
| 202888_s_at | ANPEP | alanyl (membrane) aminopeptidase |
| 223484_at | C15orf48 | chromosome 15 open reading frame 48 |
| 1553920_at | C9orf84 | chromosome 9 open reading frame 84 |
| 1554786_at | CASS4 | Cas scaffolding protein family member 4 |
| 204103_at | CCL4 | chemokine (C-C motif) ligand 4 |
| 214710_s_at | CCNB1 | cyclin B1 |
| 202705_at | CCNB2 | cyclin B2 |
| 266_s_at | CD24 | CD24 molecule |
| 209771_x_at | CD24 | CD24 molecule |
| 203799_at | CD302 | CD302 molecule |
| 209795_at | CD69 | CD69 molecule |
| 210895_s_at | CD86 | CD86 molecule |
| 210559_s_at | CDC2 | cell division cycle 2, G1 to S and G2 to M |
| 206676_at | CEACAM8 | carcinoembryonic antigen-related cell adhesion molecule 8 |
| 218542_at | CEP55 | centrosomal protein 55 kDa |
| 204170_s_at | CKS2 | CDC28 protein kinase regulatory subunit 2 |
| 219890_at | CLEC5A | C-type lectin domain family 5, member A |
| 221698_s_at | CLEC7A | C-type lectin domain family 7, member A |
| 208146_s_at | CPVL | carboxypeptidase, vitellogenic-like |
| 205931_s_at | CREB5 | cAMP responsive element binding protein 5 |
| 205898_at | CX3CR1 | chemokine (C-X3-C motif) receptor 1 |
| 1568934_at | CX3CR1 | chemokine (C-X3-C motif) receptor 1 |
| 202887_s_at | DDIT4 | DNA-damage-inducible transcript 4 |
| 205000_at | DDX3Y | DEAD (Asp-Glu-Ala-Asp) box polypeptide 3, Y-linked |
| 224327_s_at | DGAT2 | diacylglycerol O-acyltransferase homolog 2 (mouse) |
| 231886_at | DKFZP434B2016 | similar to hypothetical protein LOC284701 |
| 235341_at | DNAJC3 | DnaJ (Hsp40) homolog, subfamily C, member 3 |
| 206871_at | ELA2 | elastase 2, neutrophil |
| 210724_at | EMR3 | egf-like module containing, mucin-like, hormone receptor-like 3 |
| 231029_at | F5 | coagulation factor V (proaccelerin, labile factor) |
| 202345_s_at | FABP5/ FABP5L2/ FABP5L7 | fatty acid binding protein 5 (psoriasis-associated)/ fatty acid binding protein 5-like 2/ fatty acid binding protein 5-like 7 |
| 204834_at | FGL2 | fibrinogen-like 2 |
| 227265_at | FGL2 | fibrinogen-like 2 |
| 220326_s_at | FLJ10357 | hypothetical protein FLJ10357 |
| 241627_x_at | FLJ10357 | hypothetical protein FLJ10357 |
| 58780_s_at | FLJ10357 | hypothetical protein FLJ10357 |
| 204072_s_at | FRY | furry homolog (*Drosophila*) |
| 224148_at | FYB | FYN binding protein (FYB-120/130) |
| 213524_s_at | G0S2 | G0/G1switch 2 |
| 204222_s_at | GLIPR1 | GLI pathogenesis-related 1 |
| 207651_at | GPR171 | G protein-coupled receptor 171 |
| 228949_at | GPR177 | G protein-coupled receptor 177 |
| 210164_at | GZMB | granzyme B (granzyme 2, cytotoxic T-lymphocyte-associated serine esterase 1) |
| 206643_at | HAL | histidine ammonia-lyase |
| 202581_at | HSPA1A/ HSPA1B | heat shock 70 kDa protein 1A/ heat shock 70 kDa protein 1B |
| 206976_s_at | HSPH1 | heat shock 105 kDa/110 kDa protein 1 |
| 208200_at | IL1A | interleukin 1, alpha |
| 211506_s_at | IL8 | interleukin 8 |
| 206700_s_at | JARID1D | jumonji, AT rich interactive domain 1D |
| 204444_at | KIF11 | kinesin family member 11 |
| 224534_at | KREMEN1 | kringle containing transmembrane protein 1 |
| 218963_s_at | KRT23 | keratin 23 (histone deacetylase inducible) |
| 212531_at | LCN2 | lipocalin 2 |
| 1558920_at | LOC100128590 | hypothetical protein LOC100128590 |
| 230292_at | LOC100131993 | Similar to hCG2020760 |
| 201909_at | LOC100133662/ RPS4Y1 | hypothetical protein LOC100133662/ ribosomal protein S4, Y-linked 1 |

TABLE 1-continued

List of 117 candidate biomarker gene probes.

| Affymetrix ID | Gene Symbol | Description |
|---|---|---|
| 1558882_at | LOC401233 | similar to HIV TAT specific factor 1; cofactor required for Tat activation of HIV-1 transcription |
| 244065_at | LOC643827 | similar to cell recognition molecule CASPR3 |
| 205114_s_at | LOC728830/ CCL3L1/ CCL3/ CCL3L3 | chemokine (C-C motif) ligand 3/ chemokine (C-C motif) ligand 3-like 1/ chemokine (C-C motif) ligand 3-like 3/ similar to C-C motif chemokine 3-like 1 precursor (Small-inducible cytokine A3-like 1) (Tonsillar lymphocyte LD78 beta protein) (LD78-beta(1-70)) (G0/G1 switch regulatory protein 19-2)(G0S19-2 protein) (PAT 464.2) |
| 205114_s_at | LOC728830/ CCL3L1/ CCL3/ CCL3L3 | chemokine (C-C motif) ligand 3/ chemokine (C-C motif) ligand 3-like 1/ chemokine (C-C motif) ligand 3-like 3/ similar to C-C motif chemokine 3-like 1 precursor (Small-inducible cytokine A3-like 1) (Tonsillar lymphocyte LD78 beta protein) (LD78-beta(1-70)) (G0/G1 switch regulatory protein 19-2) (G0S19-2 protein) (PAT 464.2) |
| 202018_s_at | LTF | lactotransferrin |
| 36711_at | MAFF | v-maf musculoaponeurotic fibrosarcoma oncogene homolog F (avian) |
| 220945_x_at | MANSC1 | MANSC domain containing 1 |
| 210484_s_at | MGC31957/ TNFRSF10C | hypothetical protein MGC31957/ tumor necrosis factor receptor superfamily, member 10c, decoy without an intracellular domain |
| 203435_s_at | MME | membrane metallo-endopeptidase |
| 203434_s_at | MME | membrane metallo-endopeptidase |
| 231688_at | MMP8 | matrix metallopeptidase 8 (neutrophil collagenase) |
| 207329_at | MMP8 | matrix metallopeptidase 8 (neutrophil collagenase) |
| 217546_at | MT1M | metallothionein 1M |
| 204162_at | NDC80 | NDC80 homolog, kinetochore complex component (*S. cerevisiae*) |
| 213915_at | NKG7 | natural killer cell group 7 sequence |
| 236930_at | NUMB | Numb homolog (*Drosophila*) |
| 218039_at | NUSAP1 | nucleolar and spindle associated protein 1 |
| 205041_s_at | ORM1/ ORM2 | orosomucoid 1/ orosomucoid 2 |
| 206470_at | PLXNC1 | plexin C1 |
| 218009_s_at | PRC1 | protein regulator of cytokinesis 1 |
| 242482_at | PRKAR1A | protein kinase, cAMP-dependent, regulatory, type I, alpha (tissue specific extinguisher 1) |
| 220570_at | RETN | resistin |
| 216834_at | RGS1 | regulator of G-protein signaling 1 |
| 202388_at | RGS2 | regulator of G-protein signaling 2, 24 kDa |
| 230720_at | RNF182 | ring finger protein 182 |
| 204669_s_at | RNF24 | ring finger protein 24 |
| 209267_s_at | SLC39A8 | solute carrier family 39 (zinc transporter), member 8 |
| 1556583_a_at | SLC8A1 | solute carrier family 8 (sodium/calcium exchanger), member 1 |
| 224724_at | SULF2 | sulfatase 2 |
| 201506_at | TGFBI | transforming growth factor, beta-induced, 68 kDa |
| 201109_s_at | THBS1 | thrombospondin 1 |
| 201110_s_at | THBS1 | thrombospondin 1 |
| 211163_s_at | TNFRSF10C | tumor necrosis factor receptor superfamily, member 10c, decoy without an intracellular domain |
| 206222_at | TNFRSF10C | tumor necrosis factor receptor superfamily, member 10c, decoy without an intracellular domain |
| 201292_at | TOP2A | topoisomerase (DNA) II alpha 170 kDa |
| 201291_s_at | TOP2A | topoisomerase (DNA) II alpha 170 kDa |
| 204822_at | TTK | TTK protein kinase |
| 202589_at | TYMS | thymidylate synthetase |
| 228492_at | USP9Y/ LOC100130216 | hypothetical protein LOC100130216/ ubiquitin specific peptidase 9, Y-linked (fat facets-like, *Drosophila*) |
| 204026_s_at | ZWINT | ZW10 interactor |
| 236552_at | N/A | N/A |
| 1561654_at | N/A | N/A |
| 243170_at | N/A | N/A |
| 232555_at | N/A | N/A |
| 1556923_at | N/A | N/A |
| 244218_at | N/A | N/A |
| 239102_s_at | N/A | N/A |
| 238170_at | N/A | N/A |
| 241041_at | N/A | N/A |
| 1570194_x_at | N/A | N/A |
| 217521_at | N/A | N/A |
| 239021_at | N/A | N/A |
| 227618_at | N/A | N/A |
| 239464_at | N/A | N/A |
| 1566964_at | N/A | N/A |
| 232958_at | N/A | N/A |
| 230585_at | N/A | N/A |
| 216782_at | N/A | N/A |

TABLE 1-continued

List of 117 candidate biomarker gene probes.

| Affymetrix ID | Gene Symbol | Description |
| --- | --- | --- |
| 234640_x_at | N/A | N/A |
| 234632_x_at | N/A | N/A |

Of these 117 candidate biomarker gene probes, a number of stratification biomarkers were selected for further study based on a priori criteria: 1) the gene has biological and mechanistic plausibility regarding the host response to infection, immunity, and/or inflammation, and 2) the gene product (i.e. protein) is readily measured in the blood compartment. Based on these two criteria, a final working list of 15 candidate biomarker genes was derived, as shown in Table 2.

TABLE 2

Final working list of 15 candidate biomarker gene probes.

| Gene Symbol | Description |
| --- | --- |
| CCL3 | C-C chemokine ligand 3; a.k.a. MIP-1α |
| LCN2 | Lipocalin 2; a.k.a. NGAL |
| MMP8 | Matrix metallopeptidase 8; a.k.a. neutrophils collagenase |
| RETN | Resistin |
| THBS | Thrombospondin 1 |
| GZMB | Granzyme B |
| HSPA1B | Heat shock protein 70 kDa 1B |
| ORM1 | Orosomucoid 1, acute phase protein with unknown function |
| CCL4 | C-C chemokine ligand 3; a.k.a. MIP-1β |
| IL8 | Interleukin-8 |
| LTF | Lactotransferrin |
| ELA2 | Neutrophil elastase 1 |
| IL1A | Interleukin 1α |
| SULF2 | Sulfatase 2; extracellular modulator of heparan sulfate proteoglycans |
| FGL2 | Fibrinogen-like 2; acute phase protein similar to fibrinogen |

*Median of non-survivors relative to median of survivors.

Of the 15 candidate biomarker gene probes listed in Table 2, 12 biomarker gene probes were measured from patient serum samples, as listed in Table 3. The 12 candidate biomarkers (gene symbols) included: C-C chemokine ligand 3 (CCL3), C-C chemokine ligand 4 (CCL4), neutrophil elastase 2 (ELA2), granzyme B (GZMB), heat shock protein 70 kDa 1B (HSPA1B), interleukin 1α (IL1A), interleukin 8 (IL8), lipocalin 2 (LCN2), lactotransferrin (LTF), matrix metallopeptidase 8 (MMP8), resistin (RETN), and thrombospondin 1 (THBS1).

TABLE 3

List of 12 biomarker gene probes selected for panel.

| Gene Symbol | Description |
| --- | --- |
| CCL3 | C-C chemokine ligand 3; a.k.a. MIP-1α |
| LCN2 | Lipocalin 2; a.k.a. NGAL |
| MMP8 | Matrix metallopeptidase 8; a.k.a. neutrophils collagenase |
| RETN | Resistin |
| THBS | Thrombospondin 1 |
| GZMB | Granzyme B |
| HSPA1B | Heat shock protein 70 kDa 1B |
| CCL4 | C-C chemokine ligand 3; a.k.a. MIP-1β |
| IL8 | Interleukin-8 |

TABLE 3-continued

List of 12 biomarker gene probes selected for panel.

| Gene Symbol | Description |
| --- | --- |
| LTF | Lactotransferrin |
| ELA2 | Neutrophil elastase 1 |
| IL1A | Interleukin 1α |

The plasma concentrations of the candidate biomarkers were measured using a multi-plex magnetic bead platform (MILLIPLEX™ MAP) designed for this project by the EMD Millipore Corporation (Billerica, Mass.). Biomarker concentrations were measured in a Luminex® 100/200 System (Luminex Corporation, Austin, Tex.), according the manufacturer's specifications. Technical assay performance data have previously been reported (Wong, et al. *Crit. Care,* 16:R174 (2012)).

Additional Stratification Variables

Several data elements were abstracted for consideration in the risk modeling that could potentially be associated with poor outcomes: serum lactate concentration (mmol/L) at study entry, age, gender, and APACHE II/III score. The presence of the following co-morbid conditions was also recorded: New York Heart Association Class IV congestive heart failure (NYHA Class IV CHF), chronic obstructive pulmonary disease (COPD), requirement for chronic dialysis, chronic hepatic failure, and requirement for chronic steroids at study entry. A "chronic disease" variable was also derived, defined as positive in the presence of any one of these co-morbidities.

Example 2

Statistical Analysis

Data were initially described using medians, interquartile ranges, frequencies, and percents. Comparisons between survivors (negative cases) and non-survivors (positive cases) used the Mann-Whitney U-test, Chi-square, or Fisher's Exact tests as appropriate. Descriptive statistics and comparisons used SigmaStat Software (Systat Software, Inc., San Jose, Calif.).

To derive the decision tree, a classification and regression tree (CART) approach was employed for the determination of biomarker cutoffs, as well as cutoffs for other potential predictor variables (Che, et al. *Adv. Exp. Med. Biol.* 696:191-9 (2011); Muller, et al. *Clin. Chim. Acta* 394:1-6 (2008)). CART analysis represents a powerful approach for discovering complex predictor variable interactions that may not be evident using more traditional approaches (Che, et al. *Adv. Exp. Med. Biol.* 696:191-9 (2011); Muller, et al. *Clin. Chim. Acta* 394:1-6 (2008)).

The primary outcome variable for the modeling procedures was all-cause 28-day mortality, without consideration of the treatment arm, in the derivation cohort. All biomarker data were derived from plasma samples obtained at study entry (i.e. within 24 hours of meeting criteria for septic shock/severe sepsis).

The CART analysis procedure considered all 12 candidate biomarkers, as well as the other potential clinical predictor variables listed above. The tree was built using Salford Predictive Modeler v6.6 (Salford Systems, San Diego, Calif.). Performance of the tree was determined using diagnostic test statistics with 95% confidence intervals computed using the score method as implemented by VassarStats Website for Statistical Computation (http<colon> slash slash>faculty<dot>vassar<dot>edu<slash>lowry<slash>VassarStats<dot>html). The area under the receiver operating characteristic (ROC) curve for predicting mortality using the biomarker-based model was compared to that of the APACHE II and APACHE III scores, using the method of Hanley and McNeil to take into account the lack of independence between the two different methods, under a nonparametric assumption (Hanley, et al. *Radiology* 148:839-43 (1983)). (1983)).

Example 3

Derivation of the Biomarker-Based Model

Table 4 provides the clinical and demographic data for the derivation cohort (n=341), all of whom had septic shock. The 109 (32.0%) non-survivors were older and a higher median APACHE II score; a higher proportion also had chronic disease at study entry, compared to the 232 survivors. The mean and median times to death in the derivation cohort non-survivors were 8.7±7.9 (S.D.) and 6 (IQR 2 to 13) days, respectively.

TABLE 4

Clinical and demographic data for the derivation and test cohorts.

| | Derivation Cohort | | | Test Cohort 1 | |
|---|---|---|---|---|---|
| | All | Survivors | Non-survivors | All | Survivors |
| N | 341 | 232 | 109 | 331 | 232 |
| Median age (IQR) | 63 (51-73) | 61 (48-72) | 64 (54-76)[3] | 61 (50-72) | 58 (47-69) |
| Males, N (%) | 201 (58.9) | 142 (61.2) | 59 (54.1) | 229 (69.2)[5] | 164 (70.7) |
| Median APACHE II (IQR)[1] | 27 (22-32) | 25 (20-30) | 31 (24-35)[3] | 23 (18-29)[6] | 22 (17-27) |
| N with chronic disease (%)[2] | 165 (48.4) | 96 (41.4) | 69 (63.3)[4] | 95 (28.7)[5] | 56 (24.1) |
| Mean days to death ± S.D. | n/a | n/a | 8.7 ± 7.9 | n/a | n/a |
| Median days to death (IQR) | n/a | n/a | 6 (2-13) | n/a | n/a |
| N with septic shock (%) | 341 (100) | 232 (100) | 109 (100) | 271 (81.9)[5] | 182 (78.4) |

| | Test Cohort 1 Non-survivors | Test Cohort 2 | | |
|---|---|---|---|---|
| | | All | Survivors | Non-survivors |
| N | 109 | 209 | 121 | 88 |
| Median age (IQR) | 69 (56-76)[3] | 62 (51-71) | 63 (50-72) | 62 (53-71) |
| Males, N (%) | 65 (59.6)[4] | 116 (55.5) | 67 (55.3) | 49 (55.7) |
| Median APACHE II (IQR)[1] | 27 (20-32)[3] | 50 (37-79) | 51 (37-76) | 50 (38-82) |
| N with chronic disease (%)[2] | 39 (35.8)[4] | 132 (63.2)[5] | 68 (56.2) | 64 (74.4)[4] |
| Mean days to death ± S.D. | 11.1 ± 8.0[6] | n/a | n/a | 7.5 ± 6.9 |
| Median days to death (IQR) | 10 (4-17)[6] | n/a | n/a | 5 (2-11) |
| N with septic shock (%) | 89 (81.7) | 209 (100) | 121 (100) | 88 (100) |

[1]The derivation cohort and test cohort 1 had APACHE II scores recorded, whereas test cohort 2 had APACHE III scores recorded.
[2]The presence of at least one of the following at study entry: New York Heart Association Class 4 congestive heart failure, chronic obstructive pulmonary disease, requirement for chronic dialysis, chronic hepatic failure, or requirement for chronic steroids.
[3]$p < 0.05$ vs. respective survivors; rank sum test.
[4]$p < 0.05$ vs. respective survivors; chi square.
[5]$p < 0.05$ vs. derivation cohort; chi square.
[6]$p < 0.05$ vs. derivation cohort; rank sum test.

FIG. 1 depicts the derived decision tree. Maximum accuracy was achieved with five of the 12 candidate stratification biomarkers, namely CCL3, HSPA1B, IL8, GZMB, and CCL4. Serum lactate concentration at study entry and the presence/absence of chronic disease further improved predictive accuracy. There were six low risk terminal nodes (0.0 to 12.5% risk of death; terminal nodes 1, 3, 5, 7, 8, and 10) and six high-risk terminal nodes (34.4 to 84.2% risk of death; terminal nodes 2, 4, 6, 9, 11, and 12).

Of the 138 subjects classified as low risk, 131 survived (94.9%), and 7 (4.1%) had died by 28 days. Of the 203 subjects classified as high risk, 102 (50.2%) had died by 28 days. Table 5 shows the diagnostic test characteristics of the decision tree in the derivation cohort.

TABLE 5

Diagnostic test characteristics of the decision trees.

|  | Derivation Cohort | Test Cohort 1 | Calibration Cohort | Test Cohort 2 |
| --- | --- | --- | --- | --- |
| Subjects # | 341 | 331 | 672 | 209 |
| True Positives # | 102 | 87 | 182 | 75 |
| True Negatives # | 131 | 114 | 291 | 73 |
| False Positives # | 101 | 118 | 173 | 48 |
| False Negatives # | 7 | 12 | 26 | 13 |
| Sensitivity | 94% (87-97)[1] | 88% (79-93) | 88% (82-92) | 85% (76-92) |
| Specificity | 56% (50-63) | 49% (43-56) | 63% (58-67) | 60% (51-69) |
| Pos. Predictive Value | 50% (43-57) | 42% (36-50) | 51% (46-57) | 61% (52-70) |
| Neg. Predictive Value | 95% (89-98) | 90% (84-95) | 92% (88-94) | 85% (75-91) |
| +Likelihood Ratio | 2.1 (1.8-2.5) | 1.7 (1.5-2.0) | 2.3 (2.1-2.7) | 2.1 (1.7-2.7) |
| −Likelihood Ratio | 0.1 (0.06-0.2) | 0.2 (0.1-0.4) | 0.2 (0.1-0.3) | 0.2 (0.1-0.4) |
| Area Under the Curve | 0.834 (0.792-0.875) | 0.720 (0.661-0.780) | 0.793 (0.758-0.823) | 0.726 (0.660-0.792) |

[1]Numbers in parentheses represent 95% confidence intervals.

Example 4

Validation of the Biomarker-Based Model

Independent test cohort 1 consisted of 331 subjects with septic shock (81.9%) or severe sepsis (18.1%), of whom 99 (29.9%) did not survive to 28 days. Table 4 provides the clinical and demographic data for test cohort 1. Compared to the derivation cohort, test cohort 1 had a higher proportion of male subjects, a lower median APACHE II score, a lower proportion of subjects with a chronic disease, and a lower proportion of subjects with septic shock. The mortality rate of test cohort 1 (29.9%) was not significantly different compared to the derivation cohort (32.0%). Within test cohort 1, non-survivors had a higher median age, a lower proportion of male subjects, a higher median APACHE II score, and a higher proportion of subjects with chronic disease, compared to the survivors.

The mean and median times to death in test cohort 1 non-survivors were 11.1±8.0 and 10 (IQR 4 to 17) days, respectively, both of which were significantly greater compared to the derivation cohort.

FIG. 2 depicts the classification of test cohort 1 subjects according to the decision tree. Of the test cohort 1 subjects, 126 were classified as low risk (terminal nodes 1, 3, 5, 7, 8, and 10), while 205 were classified as high risk (terminal nodes 2, 4, 6, 9, 11, and 12). Among the low-risk subjects, the mortality rate was 9.5%, while the mortality rate was 42.4% among the high-risk subjects. Table 5 shows the diagnostic test characteristics of the decision tree in test cohort 1. The model did not perform differently when tested against only the test cohort subjects with septic shock (n=271).

Example 5

Comparison to Apache II

A subsequent analysis was conducted to compare the performance of the biomarker-based model for all subjects in the derivation cohort and test cohort 1 (n=672) to that of APACHE II. FIG. 3 depicts the ROC curves for the biomarker-based model and APACHE II, based on the respective probabilities of death. The area under the curve (AUC) for the biomarker-based model (0.784, 95% CI: 0.747-0.820) was significantly greater than that of APACHE II (0.676; 95% CI: 0.632-0.721; p=0.0001).

To assess further whether the biomarker-based model improves classification beyond that of APACHE II, the net reclassification index (NRI) was calculated. The NRI is a measure of how much the accuracy of predicted outcomes is improved when adding information and ranges between −2 and +2. A score of −2 indicates that all true positives are reclassified as false negatives, all true negatives are reclassified as false positives, and no false classifications are reclassified as true classifications. Conversely, when the score is +2, adding the information correctly reclassifies every case.

When adding the information from the biomarker-based model to the information in APACHE II, the NRI was 0.576 (95% CI: 0.341-0.812), thus indicating a significant overall improvement in final patient classification. In other words, the biomarker-based model provides additional classification capacity beyond the information included in APACHE II.

Example 6

Model Calibration

The decision tree was calibrated by combining all subjects in the derivation cohort and test cohort 1 (n=672). The calibrated decision tree is depicted in FIG. 4.

Notable changes in the calibrated tree include the addition of IL1A as a lower level decision rule leading to terminal nodes 7 and 8 and the replacement of GZMB-based terminal nodes 4 and 5 with an IL8-based decision rule. In addition, the decision rules in the center of the tree, based on lactate and chronic disease status, changed their relative level positions.

The calibrated tree contains six low risk terminal nodes (2.7 to 17.4% risk of death; terminal nodes 1, 3, 4, 6, 8, and 10) and six high risk terminal nodes (45.3 to 75.0% risk of death; terminal nodes 2, 5, 7, 9, 11, and 12). Of the 317 subjects classified as low risk, 291 survived (91.8%), and 26 (8.9%) had died by 28 days. Of the 355 subjects classified as high risk, 182 (51.3%) had died by 28 days. Table 5 depicts the diagnostic test characteristics of the calibrated decision tree.

Example 7

Testing the Calibrated Decision Tree

The calibrated decision tree was tested using independent test cohort 2, which consisted of 209 subjects with septic shock, of whom 88 (42.1%) did not survive to 28 days. Table 4 provides the clinical and demographic data for test cohort 2.

Compared to the derivation cohort, test cohort 2 had a higher mortality rate and a higher proportion of subjects with chronic disease. Within test cohort 2, non-survivors had a higher proportion of subjects with chronic disease, compared to the survivors. The mean and median times to death in the test cohort 2 non-survivors were 7.5±6.9 and 5 (IQR 2 to 11) days, respectively, neither of which was significantly compared to the derivation cohort.

FIG. 5 depicts the classification of the test cohort 2 subjects according to the calibrated decision tree. Of the test cohort 2 subjects, 86 were classified as low risk (terminal nodes 1, 3, 4, 6, 8, and 10), while 123 were classified as high risk (terminal nodes 2, 5, 7, 9, 11, and 12). Among the low-risk subjects, the mortality rate was 15.1%, while among the high-risk subjects the mortality rate was 60.9%. Table 5 depicts the diagnostic test characteristics of the calibrated decision tree in test cohort 2.

Since test cohort 2 had APACHE III data available, the performance of the calibrated model was compared with that of APACHE III, using the respective probabilities of death. In test cohort 2, the AUC for the calibrated model was 0.726 (95% CI: 0.660-0.792), whereas the AUC for APACHE III was 0.514 (95% CI: 0.434-0.595; p<0.0001).

Example 8

Use of the Biomarker-Based Decision Tree to Predict an Outcome for an Adult Patient with Septic Shock The method is carried out on a patient to predict an outcome for an adult patient with septic shock. A serum sample is obtained from an adult patient. Serum concentrations of CCL3, HSPA1B, IL8, GZMB, CCL4, IL1A and serum lactate concentration are then measured (e.g. using a magnetic bead multi-plex platform and a Luminex® 100/200 System), the presence or absence of chronic disease is determined, defined as the presence or absence of at least one of the following co-morbidities: congestive heart failure (NYHA Class IV CHF), chronic obstructive pulmonary disease (COPD), requirement for chronic dialysis, chronic hepatic failure, requirement for chronic steroids, and hematologic or metastatic solid organ malignancy, and the patient's age is noted. The results from the serum concentrations of CCL3, HSPA1B, IL8, GZMB, CCL4, IL1A, and serum lactate concentration, the presence or absence of chronic disease, and the patient's age are then subjected to the decision tree described herein in order to predict an outcome for an adult patient with septic shock.

Example 9

Use of the Biomarker Based Decision Tree to Enhance Clinical Trial Design

A serum sample is obtained from an adult patient. Serum concentrations of CCL3, HSPA1B, IL8, GZMB, CCL4, and IL1A and serum lactate concentration are then measured (e.g. using a magnetic bead multi-plex platform and a Luminex® 100/200 System), the presence or absence of chronic disease is determined, defined as the presence or absence of at least one of the following co-morbidities: congestive heart failure (NYHA Class IV CHF), chronic obstructive pulmonary disease (COPD), requirement for chronic dialysis, chronic hepatic failure, requirement for chronic steroids, and hematologic or metastatic solid organ malignancy, and the patient's age is noted. The results from the serum concentrations of CCL3, HSPA1B, IL8, GZMB, CCL4, IL1A, and serum lactate concentration, the presence or absence of chronic disease, and the patient's age are then used to subject the patient to the biomarker-based decision tree described herein in order to classify the patient into an outcome risk category, based on the model: low risk ($\leq 18\%$ mortality probability), moderate risk (18 to 40% mortality probability), and high risk ($\geq 40\%$ mortality probability). The patient's risk level is then used to qualify or disqualify the patient from one or more high risk clinical trials. For example, patients classified as high risk are then determined to be suitable candidates for high risk clinical trials, and patients classified as low risk are then determined to be poor candidates for high risk clinical trials.

Example 10

Use of the Biomarker Based Decision Tree to Stratify Clinical Trial Patients

One or more serum samples is obtained from one or more adult patients enrolled in a clinical trial. Serum concentrations of CCL3, HSPA1B, IL8, GZMB, CCL4, and IL1A and serum lactate concentration are then measured (e.g. using a magnetic bead multi-plex platform and a Luminex® 100/200 System), the presence or absence of chronic disease is determined, defined as the presence or absence of at least one of the following co-morbidities: congestive heart failure (NYHA Class IV CHF), chronic obstructive pulmonary disease (COPD), requirement for chronic dialysis, chronic hepatic failure, requirement for chronic steroids, and hematologic or metastatic solid organ malignancy, and the patient's age is noted. The results from the serum concentrations of CCL3, HSPA1B, IL8, GZMB, CCL4, IL1A, and serum lactate concentration, the presence or absence of chronic disease, and the patient's age are then used to subject the patient to the biomarker-based decision tree described herein in order to classify the patient into an outcome risk category, based on the model: low risk ($\leq 18\%$ mortality probability), moderate risk (18 to 40% mortality probability), and high risk ($\geq 40\%$ mortality probability). The risk levels of the one or more patients are then used for stratified analysis, wherein the clinical trial results are analyzed based on risk stratification.

The various methods and techniques described above provide a number of ways to carry out the application. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some preferred embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

In some embodiments, the numbers expressing quantities of ingredients, properties such as molecular weight, reaction conditions, and so forth, used to describe and claim certain embodiments of the application are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

In some embodiments, the terms "a" and "an" and "the" and similar references used in the context of describing a particular embodiment of the application (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. No language in the specification should be construed as indicating any non-claimed element essential to the practice of the application.

Preferred embodiments of this application are described herein, including the best mode known to the inventors for carrying out the application. Variations on those preferred embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

What is claimed is:

1. A method of classifying an adult patient with septic shock as high risk or low risk, the method comprising:
   identifying an adult patient with septic shock;
   obtaining a sample from the patient;
   analyzing the sample to determine the level(s) of one or more biomarkers selected from the group consisting of the biomarkers listed in Table 1, wherein the one or more biomarkers comprise all of C-C chemokine ligand 3 (CCL3), heat shock protein 70 kDa 1B (HSPA1B), interleukin-8 (IL8), C-C chemokine ligand 4 (CCL4), and granzyme B (GZMB);
   determining whether the level(s) of the one or more biomarkers are elevated above a cut-off level, wherein the presence of an elevated level of one or more biomarkers associated with septic shock in adult patients indicates that the patient has an elevated likelihood of being classified as high risk and the absence of an elevated level of one or more biomarkers associated with septic shock in adult patients indicates that the patient has a reduced likelihood of being classified as high risk,
   wherein a classification of high risk comprises:
   a) an elevated level of CCL3 and a highly elevated level of IL8, or
   b) an elevated level of CCL3, a non-highly elevated level of IL8, and a highly elevated level of GZMB, or
   c) non-elevated levels of CCL3, HSPA1B, and CCL4, and an elevated level of lactate, or
   d) a non-elevated level of CCL3, elevated levels of HSPA1B and IL8, and a positive patient history of chronic disease, or
   e) non-elevated levels of CCL3, IL8, and GZMB, an elevated level of HSPA1B, and a positive patient history of chronic disease, or
   f) a non-elevated level of CCL3, an elevated level of HSPA1B, a highly elevated level of lactate, a negative patient history of chronic disease, and a patient age of older than 36 years, and
   wherein a classification of low risk comprises:
   g) non-elevated levels of CCL3, HSPA1B, and lactate, or
   h) non-elevated levels of CCL3 and HSPA1B, and elevated levels of lactate and CCL4, or
   i) non-elevated levels of CCL3 and IL8, elevated levels of HSPA1B and GZMB, and a positive patient history of chronic disease, or
   j) a non-elevated level of CCL3, an elevated level of HSPA1B, a negative patient history of chronic disease, and a patient age of 36 years or younger, or k) a non-elevated level of CCL3, a non-highly elevated level of lactate, an elevated level of HSPA1B, a negative patient history of chronic disease, and a patient age of over 36 years, or l) an elevated level of CCL3 and non-highly elevated levels of IL8 and GZMB.

2. The method of claim 1, wherein
 a) an elevated level of CCL3 corresponds to a serum CCL3 concentration greater than 107 pg/ml,
 b) an elevated level of HSPA1B corresponds to a serum HSPA1B concentration greater than 113 ng/ml,
 c) an elevated level of IL8 corresponds to a serum IL8 concentration greater than 452 pg/ml,
 d) a highly elevated level of IL8 corresponds to a serum IL8 concentration greater than 4.0 ng/ml,
 e) an elevated level of GZMB corresponds to a serum GZMB concentration greater than 21 pg/ml,
 f) a highly elevated level of GZMB corresponds to a serum GZMB concentration greater than 25 pg/ml,
 g) an elevated level of lactate corresponds to a serum lactate concentration greater than 1.25 pg/ml,
 h) a highly elevated level of lactate corresponds to a serum lactate concentration greater than 1.35 pg/ml, and
 i) an elevated level of CCL4 corresponds to a serum CCL4 concentration greater than 48 pg/ml.

3. A method of classifying an adult patient with septic shock as high risk or low risk, the method comprising:
 identifying an adult patient with septic shock;
 obtaining a sample from the patient;
 analyzing the sample to determine the level(s) of one or more biomarkers selected from the group consisting of the biomarkers listed in Table 1, wherein the one or more biomarkers comprise all of C-C chemokine ligand 3 (CCL3), heat shock protein 70 kDa 1B (HSPA1B), interleukin-8 (IL8), C-C chemokine ligand 4 (CCL4), and granzyme B (GZMB) and interleukin 1A (IL1A);
 determining whether the level(s) of the one or more biomarkers are elevated above a cut-off level, wherein the presence of an elevated level of one or more biomarkers associated with septic shock in adult patients indicates that the patient has an elevated likelihood of being classified as high risk and the absence of an elevated level of one or more biomarkers associated with septic shock in adult patients indicates that the patient has a reduced likelihood of being classified as high risk,
 wherein a classification of high risk comprises:
 a) an elevated level of CCL3 and a highly elevated level of IL8, or
 b) elevated levels of CCL3 and GZMB, and a non-highly elevated level of IL8, or
 c) non-elevated levels of CCL3, HSPA1B, and CCL4, and a highly elevated level of lactate, or
 d) non-elevated levels of CCL3 and lactate, elevated levels of HSPA1B and IL8, and a positive patient history of chronic disease, or e) a non-elevated level of CCL3, elevated levels of HSPA1B and lactate, and a patient age of older than 44 years, or
 f) non-elevated levels of CCL3 and IL1A, elevated levels of HSPA1B and lactate, and a patient age of 44 years or younger, and
 wherein a classification of low risk comprises:
 g) non-elevated levels of CCL3 and HSPA1B, and a non-highly elevated level of lactate, or
 h) non-elevated levels of CCL3 and HSPA1B, an elevated level of CCL4, and a highly elevated level of lactate, or
 i) non-elevated levels of CCL3 and lactate, an elevated level of HSPA1B, and a negative patient history of chronic disease, or
 j) non-elevated levels of CCL3, lactate, and IL8, an elevated level of HSPA1B, and a positive patient history of chronic disease, or
 k) a non-elevated level of CCL3, elevated levels of HSPA1B, lactate, and IL1A, and a patient age of 44 years or younger, or
 l) a non-elevated level of GZMB, an elevated level of CCL3, and a non-highly elevated level of IL8.

4. The method of claim 3, wherein
 a) an elevated level of CCL3 corresponds to a serum CCL3 concentration greater than 107 pg/ml,
 b) an elevated level of HSPA1B corresponds to a serum HSPA1B concentration greater than 113.000 ng/ml,
 c) an elevated level of IL8 corresponds to a serum IL8 concentration greater than 318 pg/ml,
 d) a highly elevated level of IL8 corresponds to a serum IL8 concentration greater than 4.000 ng/ml,
 e) an elevated level of GZMB corresponds to a serum GZMB concentration greater than 21 pg/ml,
 f) an elevated level of lactate corresponds to a serum lactate concentration greater than 1.35 pg/ml,
 g) a highly elevated level of lactate corresponds to a serum lactate concentration greater than 1.45 pg/ml,
 h) an elevated level of CCL4 corresponds to a serum CCL4 concentration greater than 48 ng/ml, and
 i) an elevated level of IL1A corresponds to a serum IL1A concentration greater than 0.8 pg/ml.

5. The method of claim 1, wherein the determination of whether the level(s) of the one or more biomarkers are elevated is combined with one or more additional population-based risk scores.

6. The method of claim 5, wherein the one or more population-based risk scores comprises Acute Physiology and Chronic Health Evaluation II (APACHE) and/or Sequential Organ Failure Assessment (SOFA).

7. The method of claim 1, wherein the sample is obtained within the first hour of presentation with septic shock.

8. The method of claim 1, wherein the sample is obtained within the first 48 hours of presentation with septic shock.

* * * * *